(12) United States Patent
Whitcup et al.

(10) Patent No.: US 11,622,982 B2
(45) Date of Patent: *Apr. 11, 2023

(54) METHODS OF DIAGNOSING AND TREATING DRY EYE SYNDROME AND COMPOSITIONS FOR TREATING A HUMAN EYE

(71) Applicant: Akrivista, LLC, Corona Del Mar, CA (US)

(72) Inventors: Scott Whitcup, Laguna Hills, CA (US); Orest Olejnik, Reno, NV (US); Michael Garst, Newport Beach, CA (US); Peter Simmons, Yorba Linda, CA (US)

(73) Assignee: Akrivista LLC, Corona Del Mar, CA (US)

( * ) Notice: Subject to any disclaimer, the term of this patent is extended or adjusted under 35 U.S.C. 154(b) by 206 days.

This patent is subject to a terminal disclaimer.

(21) Appl. No.: 16/638,546

(22) PCT Filed: Aug. 17, 2018

(86) PCT No.: PCT/US2018/046918
§ 371 (c)(1),
(2) Date: Feb. 12, 2020

(87) PCT Pub. No.: WO2019/036625
PCT Pub. Date: Feb. 21, 2019

(65) Prior Publication Data
US 2020/0164013 A1    May 28, 2020

Related U.S. Application Data

(60) Provisional application No. 62/547,553, filed on Aug. 18, 2017.

(51) Int. Cl.
| | |
|---|---|
| *A61P 27/04* | (2006.01) |
| *A61K 9/00* | (2006.01) |
| *A61K 36/47* | (2006.01) |
| *A61K 36/54* | (2006.01) |
| *A61K 47/44* | (2017.01) |
| *A61K 36/235* | (2006.01) |
| *A61K 9/107* | (2006.01) |
| *A61K 36/534* | (2006.01) |
| *A61K 36/61* | (2006.01) |
| *A61K 36/752* | (2006.01) |
| *A61K 47/32* | (2006.01) |
| *G01N 33/50* | (2006.01) |

(52) U.S. Cl.
CPC .......... *A61K 36/235* (2013.01); *A61K 9/0048* (2013.01); *A61K 9/1075* (2013.01); *A61K 36/47* (2013.01); *A61K 36/534* (2013.01); *A61K 36/54* (2013.01); *A61K 36/61* (2013.01); *A61K 36/752* (2013.01); *A61K 47/32* (2013.01); *A61K 47/44* (2013.01); *A61P 27/04* (2018.01); *G01N 33/50* (2013.01)

(58) Field of Classification Search
None
See application file for complete search history.

(56) References Cited

U.S. PATENT DOCUMENTS

| | | |
|---|---|---|
| 3,278,447 A | 10/1966 | McNicholas |
| 4,146,499 A | 3/1979 | Rosano |
| 4,585,656 A | 4/1986 | Rosenthal et al. |
| 5,698,219 A | 12/1997 | Valdivia et al. |
| 6,559,182 B1 | 5/2003 | Purcell |
| 6,582,718 B2 | 6/2003 | Kawashima et al. |
| 8,909,327 B1 | 12/2014 | Bosworth |
| 8,957,048 B2 | 2/2015 | Vehige et al. |
| 9,314,528 B2 | 4/2016 | Vehige et al. |
| 9,345,779 B2 | 5/2016 | Nakata et al. |
| 2003/0086986 A1 | 5/2003 | Brujin et al. |
| 2003/0109509 A1 | 6/2003 | Gamache et al. |

(Continued)

FOREIGN PATENT DOCUMENTS

| | | |
|---|---|---|
| CN | 106389218 | 2/2017 |
| EP | 0480690 A1 | 5/2003 |

(Continued)

OTHER PUBLICATIONS

Woolf, A., et al., 2. Avocado Oil, Article • Dec. 2009 DOI: 10.1016/B978-1-893997-97-4.50008-5.*
International Search Report and Written Opinion application No. PCT/US18/46918, dated Dec. 4, 2018.
Adams et al., "Inadvertent administration of Olbas oil into the eye: a surprisingly frequent presentation," Eye, Jan. 2009, 23(1): 2 pages.

(Continued)

*Primary Examiner* — H. Sarah Park
(74) *Attorney, Agent, or Firm* — Fish & Richardson P.C.

(57) ABSTRACT

In preferred embodiments the invention is directed to ocular compositions for the treatment of dry eye, methods for making such compositions, and suites comprising a plurality of different ocular compositions each having a defined composition. In preferred examples, the invention is directed to compositions comprising at least one natural oil, wherein a first member of the suite of compositions is effective in treating dry in in a first patient having a particular set of symptoms and a different second member of the suite of compositions is effective in treating dry in in a second patient having a different set of symptoms. The invention is also directed to methods of making and using the compositions, and to skin care compositions for use around the eye, such as the upper and lower eyelids having a lubricating, non-irritating base composition comprising at least one natural oil.

22 Claims, No Drawings

(56) References Cited

U.S. PATENT DOCUMENTS

| | | |
|---|---|---|
| 2005/0202097 A1 | 9/2005 | Maskin |
| 2006/0148686 A1 | 7/2006 | Xia et al. |
| 2006/0153885 A1 | 7/2006 | Korb et al. |
| 2006/0251685 A1 | 11/2006 | Yu et al. |
| 2007/0299004 A1 | 12/2007 | Acheampong et al. |
| 2010/0137252 A1 | 6/2010 | Matsumura et al. |
| 2010/0174000 A1* | 7/2010 | Sarrazin .............. A61K 8/4993 514/772.6 |
| 2012/0108658 A1 | 5/2012 | Odaka et al. |
| 2012/0201910 A1 | 8/2012 | Gore et al. |
| 2013/0090308 A1* | 4/2013 | Vehige .................. A61K 47/38 514/57 |
| 2013/0150324 A1 | 6/2013 | Simmons et al. |
| 2013/0331341 A1 | 12/2013 | Acheampong et al. |
| 2013/0331768 A1 | 12/2013 | Nichamin |
| 2014/0302146 A1 | 10/2014 | Kurose et al. |
| 2016/0143977 A1 | 5/2016 | Likitlersuang et al. |
| 2017/0014489 A1 | 1/2017 | Welch et al. |
| 2017/0143690 A1 | 5/2017 | Gadek et al. |
| 2018/0050074 A1 | 2/2018 | Whitcup et al. |

FOREIGN PATENT DOCUMENTS

| | | |
|---|---|---|
| EP | 2633852 A1 | 9/2013 |
| EP | 3266446 | 10/2018 |
| JP | 2006233398 A | 9/2006 |
| JP | 2007528897 | 10/2007 |
| JP | 2012528888 | 11/2012 |
| WO | 2006004577 A2 | 1/2006 |
| WO | 2006009112 A1 | 1/2006 |
| WO | WO 2008/106228 | 9/2008 |
| WO | WO 2016/085885 | 6/2016 |
| WO | WO 2018/035469 | 2/2018 |

OTHER PUBLICATIONS

Azeez et al., "Effects of antioxidants on the oxidative stability of vegetable oil at elevated temperature," International Journal of Applied Science and Technology, May 2013, 3(5): 9 pages.

Dutok et al., "Acute Toxicity and Dermal and Eye Irritation of the Aqueous and Hydroalcoholic Extracts of the Seeds of (Zapote) Pouteriamammosa (L.) Cronquist," The Scientific World Journal, Article ID. 2015, 642906(7).

Jeong et al., "Evaluation of acute toxicity of plant extracts, lavender, lemon eucalyptus and cassia essential oil," The Korean Journal of Pesticide Science, English Abstract, 2010, 14(4):339-346.

Pazzoti et al., "Evaluation of oxidative stability of compound oils under accelerated storage conditions," Brazilian Archives of Biology and Technology, Nov. 14, 2018, 61, 12 pages.

Said et al., "Benefits and side effects of different vegetable oil vectors on apoptosis, oxidative stress, and P2X7 cell death receptor activation," Investigative ophthalmology & visual science, Nov. 1, 2007, 48(11):5000-5006.

International Search Report and Written Opinion dated Nov. 22, 2017.

European Search Report application No. 1784222.8 PCT/US201747627, dated Apr. 6, 2020.

Office action U.S. Appl. No. 15/680,998, dated Aug. 24, 2018.

Office action U.S. Appl. No. 15/680,998, dated Jan. 28, 2019.

Abetz et al., "Development and validation of the impact of dry eye on everyday life (IDEEL) questionnaire, a patient-reported outcomes (PRO) measure for the assessment of the burden of dry eye on patients," Health Qual. Life Outcomes, 2011, 9:111.

Begley et al., "Use of the dry eye questionnaire to measure symptoms of ocular irritation in patients with aqueous tear deficient dry eye," Cornea, 2002, 21:664-670.

Bennett et al., "Ratite oils promote keratinocyte cell growth and inhibit leukocyte activation," Poultry science, Sep. 1, 2015, 94(9):2288-2296.

Bron et al., "Grading of corneal and conjunctival staining in the context of other dry eye tests," Cornea, Oct. 2003, 22:7:640-650.

De Oliveira et al., "Effect of semisolid formulation of Persea americana Mill (avocado) oil on wound healing in rats," Evidence-Based Complementary and Alternative Medicine, Jan. 1, 2013. 1-8.

European Search Report application No. 17842221.8 PCT/US2017047627, dated Apr. 6, 2020.

European Search Report application No. 18846695.7 PCT/US2018046918, dated Apr. 28, 2021, 12 pages.

FDA.gov, [online], "OTC Active Ingredients", retrieved on Jan. 21, 2021, retrieved from www.fda.gov/downloads/aboutfda/centersoffices/officeofmedicalproductsandtobacco/cder/ucm135691.pdf, 44 pages.

Foulks et al., "New testing options for diagnosing and grading dry eye disease," Am. J. Ophthalmol., 2014, 157:6:1122-1129.

Gerbacia et al., "Microemulsions: Formulation and stabilization," J. Coll. & Interface Sci., Aug. 1973, 44:242-248.

Habashy et al., "Anti-inflammatory effects of jojoba liquid wax in experimental models," Pharm Res., 2005, 51:2:95-105.

Haris Omar, "Oleuropein in olive and its pharmacological effects," Sci. Pharm., 2010, 78(2):133-154.

Ownby et al., "Expression of pro-inflammatory mediators is inhibited by an avocado/soybean unsaponifiables and epigallocatechin gallate combination," Journal of Inflammation, Dec. 1, 2014, 11(1): 7 Pages.

PCT International Preliminary Report on Patentability in International Appln. No. PCT/US2017/047627, dated Feb. 19, 2019, 12 pages.

PCT International Preliminary Report on Patentability in International Appln. No. PCT/US2018/046918, dated Feb. 18, 2020, 8 pages.

PCT International Search Report and Written Opinion in International Appln. PCT/US2017/047627, dated Nov. 22, 2017, 13 pages.

Schiffman et al., "Reliability and validity of the ocular surface disease index," Arch. Ophthalmol. 118:615-621.

Simmons et al., "Efficacy, safety, and acceptability of a lipid-based artificial tear formulation: a randomized, controlled, multicenter clinical trial," Clinical therapeutics, Apr. 1, 2015, 37(4):858-868.

Thode et al., "Current and emerging therapeutic strategies for the treatment of meibomian gland dysfunction (MGD)," Drugs, Jul. 1, 2015, 75(11):1177-1185.

Tiffany et al., "Tear film stability and tear surface tension," Curr Eye Res., 1989, 8:5:507-15.

Tiffany, "Surface tension in tears tension superficial de la lagrima," Arch. Soc. ESP Oftalmol., 2006; 81:363-366.

European Examination Report application No. 16725159.4 dated Nov. 28, 2019.

Corazza et al., "Doubtful value of patch testing for suspected contact allergy to ophthalmic products," Acta dermato-venereologica, 2005, 85(1):70-71.

FDA.gov, [online], "FDA warns that getting alcohol-based hand sanitizer in the eyes can cause serious injury," Nov. 2, 2021, retrieved on Jul. 26, 2022, retrieved from URL<https://www.fda.gov/drugs/drug-safety-and-availability/fda-warns-getting-alcohol-based-hand-sanitizer-eyes-can-cause-serious-injury#:~:text=What%20should%20health%20care%20professionals,least%2015%20to%2020%20minutes.> 6 pages.

Gao et al., "High Level of Inflammatory Cytokines in the Tears: A Bridge of Patients with Concomitant Exotropia and Dry Eye," Oxidative Medicine and Cellular Longevity, Oct. 7, 2021, 2021: 7 pages.

Guillot et al., "A study of skin and eye irritation in the rabbit due to different sources of some cosmetic raw materials (Part II)," International Journal of Cosmetic Science, Feb. 1, 1979, 1(1): 27-57.

Hysa et al., "Immunopathophysiology and clinical impact of uveitis in inflammatory rheumatic diseases: An update." European journal of clinical investigation, Aug. 2021, 51(8):e13572, 13 pages.

Kathuria et al., "Categorization of marketed artificial tear formulations based on their ingredients: a rational approach for their use," Journal of Clinical Medicine, Mar. 21, 2021, 10(6):1289, 11 pages.

Pflugfelder et al., "Biological functions of tear film," Experimental eye research, Aug. 1, 2020, 197:108115, 16 pages.

Sade de Paiva et al., "Assessing the severity of keratitis sicca with videokeratoscopic indices," Ophthalmology, Jun. 1, 2003, 110(6):1102-1109.

(56) References Cited

OTHER PUBLICATIONS

Villena et al., "Ocular inflammation models by topical application: croton-oil induced uveitis," Current eye research, Jan. 1, 1999, 18(1):3-9.
Yoon, "Topical biological agents targeting cytokines for the treatment of dry eye disease," World J Ophthalmol, May 12, 2013, 3(2): 16-19.
See et al., "Eyelid skin as a potential site for drug delivery to conjunctiva and ocular tissues," International journal of pharmaceutics, Nov. 25, 2017, 533(1): 4 pages (Abstract).

* cited by examiner

METHODS OF DIAGNOSING AND TREATING DRY EYE SYNDROME AND COMPOSITIONS FOR TREATING A HUMAN EYE

RELATED APPLICATIONS

This application claims the benefit of provisional patent application Ser. No. 62/547,553, filed Aug. 18, 2017 and is a § 371 of international patent application PCT/US2018/46918, filed Aug. 17, 2018, each of which is hereby incorporated by reference herein in its entirety.

BACKGROUND OF THE INVENTION

The present invention relates to methods of diagnosing and treating dry eye syndrome (DES) in a human eye, and to compositions designed to treat the dry eye syndrome diagnosed. More particularly, the invention relates to methods including testing to determine if a human patient has dry eye syndrome and if so, to determine the extent or severity of the dry eye syndrome in the eye or eyes of the patient; inquiring of the patient as to what sensitivities and/or other issues the patient has that may affect treating the dry eye syndrome with medication in the eye; and providing, based on the testing and inquiring, a treatment composition to treat the patient's dry eye syndrome. By "treatment composition" is meant a topical ophthalmic formulation developed as a treatment to assist in relieving the symptoms and/or causes of dry eye syndrome.

Dry eye syndrome (also called dry eye disease), or simply dry eye, is a relatively common affliction in humans, and is a condition in which a person doesn't have enough quality tears to lubricate and nourish the eye. Tears are necessary for maintaining the health of the anterior surface of the eye and for providing clear vision. With each blink of the eyelids, tears spread across the cornea. Tears provide lubrication, reduce the risk of eye infection, wash away foreign matter in the eye, and keep the surface of the eyes smooth and clear. Excess tears in the eyes flow into small drainage ducts (tear ducts) in the inner corners of the eyelids, which drain into the back of the nose.

A person afflicted with dry eye may produce too few tears and/or their tears may not have a normal composition—that is, for example, tear quality (pH, viscosity, tonicity or protein or lipid content) may vary from a normal range of values. These changes may be due to age, surgery, a result of various medical conditions, or as a side effect of a medication.

Dry eyes can occur when tear production and drainage is not in balance; however lack of sufficient tear quantity is only one cause of dry eye disease. Too few tears can also be due to evaporation caused by exposure to environmental conditions such as wind and dry climates and may be exacerbated by lack of sufficient lipid in the tears. Inflammation or other irritation of the surface of the eye may result from chronic dry eye or lead to dry eye disease, and anti-inflammatory drugs and agents having anti-inflammatory activity may also be used to treat dry eye.

Tears are made up of three layers: an outer oil layer, a middle water layer, and an inner protein layer containing mucin, a tear protein. The oil layer helps prevent evaporation of the water layer, and the mucins on the inner mucus layer help the tears spread evenly over the cornea. Deficiencies in any of these layers can cause the tears to evaporate too quickly or fail to evenly spread across the cornea. The most common form of dry eye may result when the water layer is inadequate; this condition is called keratoconjunctivitis sicca.

Dry eye is a common and often chronic problem, particularly in older adults, and may result in a relatively wide range of eye issues. For example, relatively minor eye irritation, a gritty, scratchy or burning feeling in the eyes, excessive watering (in response to irritation), blurred vision, and, permanent damage to the cornea may occur, if left untreated.

Treatments for dry eyes generally aim to restore or maintain the normal amount of tears in the eye to minimize dryness and related discomfort and to maintain eye health.

European Patent Application EP 3 266 446 A1; U.S. Patent Publication US 2016/0143977 A1; U.S. Pat. No. 9,314,528 B2; and U.S. Pat. No. 8,957,048 B2, describe ophthalmic compositions. Tiffany, J. M., Arch. Soc. ESP Oftalmol, 2006; 81:363.366 describes surface tension in tears.

Since eye discomfort is relatively common and can result from conditions other than dry eye syndrome (DES; sometimes also called DED (dry eye disease)), it is important that testing, including an evaluation of the quantity and quality of the patient's tears, be done to determine the cause of the discomfort and the extent (or severity) of the condition causing the discomfort. In many cases this type of testing is not done. Often, the person suffering eye discomfort self-medicates by instilling generic artificial tears eye drops in the afflicted eye(s). Even if the artificial tears are identified as being useful to treat dry eye, such generic artificial tears may not be effective to treat a specific patient and/or may be irritating to, uncomfortable to, and/or fail to properly address the required quality of the tears required by the specific patient.

A widely held dogma in the ophthalmic medical community is that measurable parameters of a patient's tears based on signs and symptoms are not predictive of the severity of dry eye syndrome, or its response to therapy. As a result, it is generally the practice to treat dry eye disease using a "trial and error" approach, with the treating medical professional prescribing or recommending a treatment composition, such as an artificial tear formulation or eyelid balm, and then assessing the results at a later date and either continuing to recommend the same treatment composition, or trying a different treatment composition until beneficial results are observed or reported by the patient. For example, it has been generally thought that the more severe a patient's dry eye disease, the more viscous the treatment composition should be. Therefore, a systematic and logical method for the treatment of dry eye on an individual patient basis has not been available.

Applicants have solved this problem as described herein and now show that this view is mistaken, and that dry eye disease can be treated based at least in part on an assessment of an individual patient's symptoms and tear quality, and such measurable parameters of a patient's tears as, without limitation: refractive index, surface tension, specific gravity, viscosity, tear film breakup time, tonicity and pH. The present invention is this drawn in part to the assessment of predictive sets of such parameters, and the formulation of compositions based upon patient data including these parameters that can effectively treat particularized dry eye syndrome in individual patients.

SUMMARY AND DETAILED DESCRIPTION OF THE INVENTION

In the present application unless otherwise indicated, each and every range of values (concentrations, viscosities, and the like) stated in this specification, including the claims, are intended to specifically include the entire range and not just the endpoint(s). For example, a range stated to be 0 to 10 is intended to disclose all whole numbers between 0 and 10 such as, for example 1, 2, 3, 4, etc., all fractional numbers between 0 and 10 to three significant figures, for example 1.5, 2.3, 4.57, etc., and the endpoints 0 and 10. Also, a range associated with chemical substituent groups such as, for example, "C1 to C5 hydrocarbons", is intended to specifically include and disclose C1 and C5 hydrocarbons as well as C2, C3, and C4 hydrocarbons.

New methods of diagnosing and/or treating dry eye syndrome (DES), and artificial tear compositions for treating an eye of a human afflicted with dry eye syndrome, have been discovered. Such methods and compositions provide substantial overall efficacy in providing an increased suite of suitable treatment options and yielding more desirable therapeutic effects. In addition, other important benefits are obtained employing the present methods and compositions. For example, patient safety and comfort is enhanced.

In particular, the present methods provide for reduced risks of side effects and/or allergic reactions using the methods of the invention. Medical providers, such as prescribing physicians, can advantageously select an artificial tear treatment composition from a series of differently formulated alternatives differing in their tear quality and, thus, are provided with increased flexibility in prescribing or providing artificial tear compositions useful in treating specific, different patients and patient subpopulations. The present methods can be easily practiced.

In addition, the present compositions may be conveniently provided as a suite of different artificial tear formulation options to allow the prescriber to select from among these the most suitable, e.g., most effective and compatible composition for use by the specific patient being treated.

Furthermore, dry eye syndrome can result from conditions of the eyelids, such as blepharitis inflammation, scaling, irritation or infection of the inside of the eyelids. Thus, in certain examples, the present invention is directed to a suite of different dry eye treatment formulation options to allow the prescriber to select from among these the most suitable, e.g., most effective and compatible, composition for use by the specific patient being treated, based on an assessment of the patient's sight and symptoms of DES. In this case the dry eye treatment formulation options may not be limited to "artificial tears" but may include balms, eye and foundation make-up, emulsions, and other topical formulations having a greater viscosity than that of a typical artificial tear. Thus, in some examples a more viscous eye balm, lotion, or similar composition may be applied directly to the eyelid. Applicants have discovered that certain viscosity-enhancing components of the compositions of the present invention may provide ample viscosity considerably below the commonly assumed comfort or tolerance limits for topical ocular administration of such components. Additionally, the high viscosity balms, lotions and the like are preferably formulated, if possible, to have a degree of clarity and refractive index such that they will provide reduced, or no, blurring when spread from the eyelid to the ocular surface. Preferably, high viscosity compositions may achieve reduced viscosity on an ocular surface by dilution with the patient's tears, or (in compositions having a temperature sensitive viscosity-enhancing polymer component) by a change in temperature as compared to their placement on or under the eyelid.

Some viscosity enhancing components, such as Carbopol®-type polymers, Noveon®-type polymers, and Pemulen®-type polymers have a negative charge that also permits them to adhere well to skin surfaces. Applicants have found that these compounds may be used in concentrations of about 5-fold oil-in-water or water-in-oil lower, or about 10-fold lower than many other viscosity-enhancing components, and in emulsions with oils at concentrations of less than 1% (w/v), or less than 0.5% (w/v), or less than about 0.25% (w/v), or less than about 0.2% (w/v), or less than about 0.15% (w/v), or less than about 0.1% (w/v), or less than about 0.05% (w/v), or less than about 0.02% (w/v), or less than about 0.01% (w/v).

In general, artificial tears preferably have a viscosity in a range of from about 2 centipoise (cP) to about 8 cP, whereas emulsions typically have a viscosity in a range of from about 1.2 cP to about 250 cP, or about 4 cP to about 100 cP. Gels and ointments (such as may be used in eyelid preparations for the treatment of e.g., eyelid inflammation, scaling, blepharitis, or in makeup preparations to be applied on or near the eyelids) may have a viscosity in a range of from about 100 cP to about 2000 cP or more.

In short, the present methods and compositions provide substantial overall efficiency in identifying the specific needs and concerns of the human patient involved; and addressing the needs and concerns by providing a well suited composition for each patient.

In one aspect of the present invention, the present methods involve diagnosing and treating dry eye syndrome in a human patient. Such methods comprise assessing signs and symptoms. A "symptom" is a phenomenon that is subjectively experienced by the individual affected by a disease, while a "sign" is a phenomenon that can be objectively detected by someone other than the individual affected by the disease.

Thus, for example, testing the patient's tears to determine the tear quantity and quality and whether a particular patient has dry eye syndrome is assessment of a sign. Inquiring of the patient as to the presence, degree, or extent, of sensitivity, e.g., discomfort, allergies, etc., and/or one or more other issues the patient has with regard to treating the dry eye syndrome, for example, to having eye drops, e.g., medicated eye drops, instilled into the patient's eye, constitutes an assessment of symptoms.

Various methods have been discussed for standardizing diagnostic methods for detecting dry eye syndrome. Thus, the Tear Film and Ocular Surface Society (TFOS) Dry Eye Workshop ("DEWS II") report (see, J. S. Wolffsohn et al., The Ocular Surface xxx 544-579 (2017)) indicates that dry eye disease (DED) diagnosis is multi-factorial, wherein no single test is considered a "gold standard". Applicants submit that a clinical diagnosis of dry eye disease includes an assessment of both symptoms and signs.

Symptoms

"Symptoms" may be assessed using patient questionnaires such as the Ocular Surface Disease Index (OSDI©), see Schiffman, R. M., et al., Arch. Ophthalmol. 118:615-621 (2000). The OSDI© (copyright 1995 Allergan, Inc.) is currently the most widely used questionnaire. Other surveys such as the Dry Eye Questionnaire (DEQ) (see Begley C. G., et al., Cornea, 21:664-670 (2002) and IDEEL (see Abetz L. et al., Health Qual. Life Outcomes, 9:111 (2011) may also be used, along with visual analog scales for individual symptoms such as dryness, grittiness, foreign body sensation, photophobia, etc. Most surveys add up the scores on several of these individual symptoms to yield a comprehensive score. Tests for visual disturbance and visual function (which may be more quantitative) are also used.

While questionnaires such as the OSDI are commonly used to assess the patient's symptoms, such questionnaires, which generally have questions such as: "on a scale of from 1 to 10 how severe is your eye discomfort?" are susceptible to different interpretations by different people. For example, dry eye disease is commonly most severe in the evening, and less severe in the morning. Therefore, if the question is only asked in the morning, the symptoms may be under-reported. Importantly, discomfort may occur sporadically in some patients, whereas it may be constant in others. Moderate discomfort that occurs all day, every day may be more problematic than severe pain that lasts a few seconds once every several months. This propensity for varied interpretations of the question may contribute to the low correspondence of questionnaire-based determination of symptoms with the presence and severity of dry eye disease.

As a result, Applicants believe that it is important that surveys and questionnaires used for the purpose of collecting symptoms from subjects in order to diagnose the presence or severity of dry eye disease have a temporal component, in order to determine when the reported result occurs.

Thus, an ideal a questionnaire may contain temporal questions such "How much of the time are your eyes irritated or bothersome", or a clinician or medical professional could assess the symptom over a set time period by asking questions such as "over the past 4 hours, how irritated or bothersome are your eyes".

Specific symptoms can be queried such as stinging, burning, light sensitivity, grittiness and so forth. However, since symptoms vary from patient to patient and hour to hour, a more general symptom question such as "how irritated or bothersome are your eyes" may be more predictive of disease severity.

The temporal symptom data should be combined with the non-temporal symptom data. For example, the sum of the comprehensive non-temporal symptom data may be multiplied by the sum of the comprehensive temporal symptom data, to yield a comprehensive score. Alternatively, and presently preferably, the sum of the scored non-temporal symptom data may be added to the sum of the scored temporal symptom data, to yield a comprehensive score.

Signs

Signs may be selected from a variety of parameters that have relevance to the presence of severity of DES.

Tear Film Stability may be measured by Tear Breakup Time (TBUT) and tear film evaporation rate. TBUT may be determined visually by instilling a fluorescein dye using e.g., a micropipete or a fluorescein-impregnated strip. Since controlling the volume instilled with strips may be difficult, the use of narrow (1 mm) strips and the use of dry sterile applicators have been proposed. Also tear film stability can be determined by measuring distortion of a reflected pattern, or by using an automated device capable of measuring topography and advanced external imaging such as the Oculus™ device.

Evaporation is not routinely measured in clinical practice, although a few fairly simple devices for directly or indirectly determining it are available. For example, evaporation of the tear film causes cooling of the ocular surface and infrared thermography is able to measure the temperature of the ocular surface in a non-invasive manner and provide an objective, quantitative output.

Tear Volume may be assessed with meniscometry using optical coherence tomography (OCT), the phenol red thread test, or various versions of the Schirmer test.

Tear Film Composition may be assessed using:
a) Determination of tear film osmolality, which generally increases with disease severity.
b) tear ferning tests, in which tears dried on a glass microscope slide form a characteristic "fern-like" crystal pattern, which is compact and dense in healthy eyes but absent or fragmented in diseased eyes.
c) various analytical methods to assess markers of inflammation (MMP-9 (matrix metalloaproteinase 9), lactoferrin, cytokines and chemokines, HLA-DR (Human leucocyte antigen-antigen D related)).

Ocular Surface Damage may be assessed using a number of different vital dyes (fluorescein, Rose Bengal, lissamine green) and scoring methods (for example DEWS II lists 5 different staining scoring methods).

Eyelids: Meibomian glands are assessed for function, and may be imaged by a variety of methods. Meibomian gland dysfunction is a subset of Dry Eye Disease; normally the Meibomian glands secrete meibum, an oily substance that prevents tear evaporation.

Additional innovative methods for diagnosing and characterizing DES were advanced at the 2018 meeting of the Association for Research in Vision and Ophthalmology ("ARVO 2018"). For example, Molina et al. discussed conducting a metagenomic analysis of the microbiome on the surface of the eye of healthy patients and those having DED. The results were able to determine taxonomic differences in the microbial flora that distinguish healthy subjects from those suffering from DES. Molina et al., "Metagenomic analysis of microbial species (microbiome) on the surface of the eye in DED", Posterboard B0078, Abstract No. 900-B0078 ARVO 2018 Meeting, Honolulu, Hi., (Apr. 29, 2018).

Fortinberry et al. report on the isolation and sequencing of microRNAs from extracellular vesicles in tears of subjects having the potential to regulate ocular surface inflammation associated with dry eye disease. Fortinberry et al., "RNA analysis from microvesicles released from the ocular surface—relating to inflammatory state of the eye", Posterboard B0088, Abstract No. 910-B0088 ARVO 2018 Meeting, Honolulu, 11, (Apr. 29, 2018).

Berg et al. described in a withdrawn abstract a "lab-on-a-chip" immunoassay to evaluate the analytical performance of Matrix Mellatoproteinase-9 (MMP-9) measurement as a biomarker for DES in a dry eye patient population across 8 sample levels (0, 25, 409, 100, 250, 500, and 1000 ng/ml) using a fluorescent immunoassay and a sample volume of about 100 nl. Berg et al., Analytical Performance of a Quantitative MMP-9 Tear Fluid Analysis on a Nanoliter Lab-on-a-Chip Immunoassay Platform, Posterboard B0117, Abstract No. 939-B0117 ARVO 2018 Meeting, Honolulu. Hi., (Apr. 29, 2018).

Huang et al. describe methods of measuring levels of lymphotoxin alpha (LTA) in tear film as an indication of the presence of DES. Huang et al., Measurement of lymphotoxin alpha (LTA) in tear film—reduced in DED, Posterboard B0133, Abstract No. 955-B0133 ARVO 2018 Meeting, Honolulu, Hi., (Apr. 29, 2018).

Foulks, Gary N. and Pfugfelder, Stephen C., Am. J. Ophthalmol. 157:6 1122-1129 (June 2014) review new approaches to identifying biomarkers correlating to DES and response to treatment, reported in the Table below:

| Biomarkers of Dry Eye Disease with Moderate to High Clinical Correlation or Responding to Treatment | | |
|---|---|---|
| Marker | Clinical Correlation | Reference |
| HLA-DR | Presence decreased with CsA and tofacitinib (Xeljanz ®) treatment | 45, 56 |
| MMP-9 | Symptom severity, corneal fluorescein staining, conjunctival lissamine green staining | 31 |
| Tear EGF | Ocular surface rose Bengal staining, corneal fluorescein staining, conjunctival lissamine green staining | 40, 65 |
| Tear IL-6 | Ocular surface rose bengal staining, corneal fluorescein staining, conjunctival lissamine green staining | 40, 65 |
| Tear IL-8, MIP-1α, IL-1β | Corneal fluorescein staining, conjunctival lissamine green staining. | 40 |
| Tear CXCL9, CXCL11 (I-TAC) | Basal tear secretion, keratoepitheliopathy, goblet cell density | 66 |
| Tear proteins S100A8 and A9 Lactoferrin Lipocalin | In subjects with MGD, grittiness, transient blur, eye pain and tearing, lid heaviness | 43 |
| MUG16 mRNA MUG16 cellular MUG16 tears | Tear meniscus Lissamine green staining; Dry eye symptom questionnaire Lissamine green staining | 67 |

*Correlation coefficient ≥0.35
HLA-DR = human leukocyte antigen-antagen DR, CsA = Cyclosporin A, MMP-9 = matrix metalloproteinase 9, EGF = epidermal growth factor, IL-6 = interleukin 6, IL-1 = interleukin 1, MIP-1α = macrophage inflammatory protein 1, MGD: meibomian gland disease, CXCL9 = chemokine (C-X-C motif) ligand 9, MUC = mucin.
References are as reported by footnote number in Foulks, Gary N. and Pfugfelder, Stephen C., Am. J. Ophthalmol. 157:6 1122-1129 (June 2014); the publications correlating with these footnote numbers in the cited reference are hereby each individually incorporated by reference herein in their entirety.

Exemplary Matrix

Viscosity is a physical property of tears (including artificial tear formulations) that inversely correlates with patient tolerability. Higher viscosity tends to blur the vision and a highly viscous artificial tear formulation tends to feel unpleasantly "goopy". Both of these qualities tend to cause patent compliance to be low, which is counterproductive regardless of how well the formulation may function therapeutically; the therapeutic value of an otherwise effective therapeutic agent is irrelevant if the patient will not use it.

Applicants have also discovered that patient tolerability of an artificial tear is directly proportional to its clarity (i.e., percent transmittance of light at 580 nm). A clear-appearing artificial tear formulation near the natural refractive index is more acceptable to patients than cloudy, low transmittance emulsions, which they tend to associate with blurred vision and visual disturbance.

Furthermore, the therapeutic healing effect is proportional to viscosity and inversely proportional to the surface tension. This is because artificial tears having higher viscosity tend to adhere to the ocular surface more effectively, thus protecting the ocular surface from drying effects, and thereby promoting healing. Lower surface tension allows the tear preparation to spread more effectively. An increase in lipid content (such as through the addition of certain oils) may lower the surface tension, thereby enhancing spreadability of the tear. When an oil, mixture of oils, or other tear components have an anti-inflammatory effect, this enhanced spreadability can thereby provide an enhanced anti-inflammatory effect.

In an exemplary method, ocular surface staining with fluorescein, rose Bengal, lissamine green and/or other dyes may be measured using standardized scales such as (or based on) the diagnostic test and template described by Bron et al., Grading of Corneal and Conjunctival Staining in the Context of other Dry Eye Tests, Cornea 22(7) 640-=50 (2003), in which a scale of from 1-5 is proposed.
Or one may use ocular surface staining.
Symptom
On a scale of 0-10
How irritated or bothersome are your eyes?
0=not irritated or bothersome at all
10-severely irritated and bothersome
On a scale of 0-10
How much of the day and night are your eyes irritated or bothersome?
0=not at all
10=constantly, all the time
Symptom score=severity×time with resultant score of 0-100
NOTE: As discussed, genetic tests or assessment of disease markers on the ocular surface and tears may be used to quantify sign severity.

The Applicants currently utilize a matrix in which patient tolerability is balanced with healing potential in a unique way by assessing patient symptoms and signs of disease severity. A sum conclusion of an assessment of a patient's signs (corneal staining or other objective measures of disease severity; which may be listed along the Y axis of the matrix) is characterized as either Low Sign Severity or High Sign Severity, while the sum conclusion of an assessment of the patient's symptoms (which may be listed along the X axis of the matrix) is also characterized as either Low Symptom Severity or High Symptom Severity. By "sum conclusion" is meant that, a plurality of symptoms and/or signs is assessed and graded as an indication of disease severity. Thus, the resulting matrix may appear, for example, as follows:

| MATRIX | | |
|---|---|---|
| | Low Symptom Severity | High Symptom Severity |
| Low Corneal Staining or other measure of disease severity | Formulation A Low Viscosity Standard Oil Conc. Normal Surf. Tension | Formulation B High Viscosity Standard Oil Conc. Normal Surf. Tension |
| High Corneal Staining or other measure of disease severity | Formulation C Low Viscosity High Oil Conc. Low Surf. Tension | Formulation D High Viscosity High Oil Conc. Low Surf. Tension |

Thus, 4 different artificial tear formulations may be made pursuant to this matrix:

a) Formulation A has low viscosity, a standard amount of oil, and a normal surface tension to provide both comfort and lubrication. A patient having low corneal staining has a relatively normal, intact tear film, which indicates that the surface tension of the tear film is relatively low. In Tiffany et al., CURR. EYE RES., 8(5):507-15 (May 1998) a negative correlation was found between surface tension and non-invasive tear breakup time (NIBUT) for both dry eyes and normal eyes. In this study the reported mean (+/−standard deviation) surface tension value was 43.6+/−2.7 mNewtons (N)/m for tears from normal eyes, and 49.6+/−2.2 mN/m for tears from dry eyes. All NIBUT values for tears from dry eyes were below 20 sec (8.9+/−5.1 sec, mean+/−SD, n=35) while 53% of normal values were 30 sec or over.

b) Formulation B is an artificial tear formulation in response to high symptom severity and low sign severity. The low sign severity indicates that the tear film remains relatively intact. This formulation has a higher viscosity (which can increase NIBUT and provide enhanced lubrication by helping the tear film adhere to the ocular surface), a standard amount of oil, and a normal surface tension.

c) Formulation C is an artificial tear formulation in response to low symptom severity and high sign severity. In this situation, the patient may not experience a high degree of ocular discomfort or vision impairment, but the objective signs indicate that the patient is suffering from DES. The formulation has low viscosity, but a heightened amount of oil (to prevent evaporation of the tear film), and normal surface tension.

d) Formulation D is an artificial tear formulation in response to both high symptom severity and high sign severity, and is an artificial tear having high viscosity, higher amounts of oil and lower than normal surface tension.

e) Additionally, for patients having either a) a measured tear hyper-osmolality of greater than 340 mOsms/L, or b) a decreased tear break-up time as assessed by the clinician of less than or equal to about 4 seconds, a "Formulation E" may be made available as a modification of Formulation D. Formulation E is hypo-osmolal, with high oil concentration, high viscosity and low surface tension. Additionally Formulation E may contain surface protecting agents.

As one example of such a suite of therapeutic compositions, in which Clarity (Percent Transmittance at 580 nm)/N is a measure of patient tolerability and N/ST is a measure of therapeutic efficacy, the indicated suite of therapeutic formulations may be made.

| Formulation | Viscosity (cP) | Surface Tension (dynes/cm) | % Transmittance (580 nm) | Clarity/N | N/ST |
|---|---|---|---|---|---|
| A<br>Low Viscosity<br>Standard Oil<br>Conc.<br>Normal Surf.<br>Tension | 5 | 50 | 90 | 18.00 | 0.10 |
| B<br>High Viscosity<br>Standard Oil<br>Conc.<br>Normal Surf.<br>Tension | 50 | 50 | 90 | 1.80 | 1.00 |
| C<br>Low Viscosity<br>High Oil Conc.<br>Low Surf.<br>Tension | 5 | 40 | 30 | 6.00 | 0.13 |
| D<br>High Viscosity<br>High Oil Conc.<br>Low Surf.<br>Tension | 50 | 40 | 30 | 0.60 | 1.25 |
| E<br>High Viscosity<br>High Oil Conc.<br>Low Surf.<br>Tension<br>Low osmolality<br>(less than about<br>300<br>mOsmol/L) | 50 | 40 | 30 | 0.60 | 1.25 |

Importantly, the same base Formulations A-E may be made more viscous for use as topical "eyelid tear" formulations for treatment of eyelid dryness and blepharitis. For example, a viscosity enhancer (such as, without limitation, methylcellulose (MC), hydroxypropyl methylcellulose (HPMC), hydroxyethyl cellulose (HEC), Carbopol®, Pemulen®, Noveon®, polyvinyl alcohol, polyethylene glycol, polyoxyethylene polyoxypropylene glycol (PEPPG), hyaluronic acid salts such as sodium hyaluronate, and polyvinyl pyrrolidone) may be added to the formulation to increase the viscosity of the formulation for this purpose.

These formulations may be applied to the ocular surface as an eyelid lubricant, and the active ingredients absorbed into the eyelid upon administration or, due to the thinness off the eyelid, through application to the outer surface of the eyelid—this application will allow it formulation to penetrate the eyelid and treat the ocular surface from within.

Additionally, Formulations A-E (and more viscous versions thereof) may be incorporated as part of cosmetic products such as, without limitation, makeup foundations, eye shadows, eyeliners, mascara, and the like. The therapeutically beneficial compositions will be absorbed into the skin (such as the eyelids, skin surrounding the eyes, the conjunctiva, etc.) to assist in alleviating the systems and signs of DES. Such makeup compositions may be applied to the outer surface of the eyelid (such as in eye shadow or foundation makeup) and permitted to penetrate the eyelid and lubricate the ocular surface in this manner. Additionally, since eye and skin makeup can often inadvertently get into the eyes, causing eye irritation, the present invention provides makeup compositions containing therapeutic compositions for the treatment of dry eye disease, which will alleviate some of this irritation.

Therefore, as can be seen using this exemplary matrix assessment of patient signs and symptoms, using the present methods. Based on this a treatment composition is then provided to use in the patient's eye to treat the patient's particular dry eye syndrome and tolerance to viscous ocular medications—e.g., foreign body sensation, etc.

The treatment composition provided to the patient is selected from a series of different compositions. Each of the different compositions comprises water and a hydrophobic component; very preferably the components contain at least one of a natural oil component, which may advantageously have a biocidal (antifungal, anti-parasitic, antiviral, and/or antimicrobial) activity when placed in a human eye.

In one embodiment, the hydrophobic component is selected from jojoba oil, hydrophobic derivatives thereof, avocado oil and hydrophobic derivatives thereof, olive oil and hydrophobic derivatives thereof, oleuropein and hydrophobic derivatives thereof, tea tree oil and hydrophobic derivatives thereof, cottonseed oil and hydrophobic derivatives thereof, sunflower oil and hydrophobic derivatives thereof, maize oil and hydrophobic derivatives thereof, linseed oil and hydrophobic derivatives thereof, rapeseed oil and hydrophobic derivatives thereof, argan oil and hydrophobic derivatives thereof, castor oil and hydrophobic derivatives thereof, soybean oil and hydrophobic derivatives thereof, caraway oil and hydrophobic derivatives thereof, rosemary oil and hydrophobic derivatives thereof, peppermint oil and hydrophobic derivatives thereof, sunflower oil and hydrophobic derivatives thereof, *Eucalyptus* oil and hydrophobic derivatives thereof, bergamot oil and hydrophobic derivatives thereof, fennel oil and hydrophobic derivatives thereof, sesame oil and hydrophobic derivatives thereof, *Ginseng* oil and hydrophobic derivatives thereof, jujube oil and hydrophobic derivatives thereof, okra oil and hydrophobic derivatives thereof, bergamot oil and hydrophobic derivatives thereof, menthol oil and hydrophobic derivatives thereof, one or more other natural oils, hydrophobic derivatives of the one or more other natural oils and mixtures of any of these oils.

By "derivative" is meant a chemical compound of composition that is, or contains a moiety that is, structurally similar to the reference compound. Thus, a "derivative" according to this definition may in certain circumstances include a synthetic precursor to, as well as a compound derived from, the reference compound.

Preferably the therapeutic compositions of the present invention comprise avocado oil or a derivative thereof, either alone or in combination with another natural oil. Even more preferable, the therapeutic compositions comprise a combination of an avocado oil and castor oil.

In another embodiment the therapeutic compositions comprise castor oil and at least one additional oil, such as a mineral oil or a plant-based oil.

In certain examples the hydrophobic components may also advantageously have anti-inflammatory and other beneficial effect, such as A) reduction of edema induced by inflammatory agents, reduction of neutrophil infiltration, reduction or amelioration of histopathological changes caused by croton oil, reduction of nitric oxide (NO) and tumor necrosis factor-alpha (TNF-alpha) release. For example, various studies have shown the anti-inflammatory activity of jojoba liquid wax. Habashy et al., Pharm Res. 51(2):95-105 (February 2005).

B) anti-inflammatory activity in osteoarthritis models as shown by decreased gene expression of interleukin-beta (IL-1B), TNF-alpha, coclooxygenase-2 (COX-2) and interleukin-8 (IL-8), decreased prostaglandin E2 (PGE2) synthesis, and inhibition of translocation of nuclear factor kappa beta (NF-kB) in articular chondrocytes from equine carpal joints following incubation with avocado/soybean unsaponifibles and epigallocatechin gallate (ECG) and subsequent activation with TNF-alpha and IL-1beta, Ownby et al., J. Inflamm. 28(11):8 (Mar. 28, 2014);

C) increased wound healing and anti-inflammatory activity of avocado oil on incisional and excisional cutaneous wound models reported in Wistar rats. De Oliveira et al., Evid. Based Complement. Internal. Med., 2013:472382 (2013):

D) anti-inflammatory activity of omega-3-fatty acids applied in compresses to the eyelids against meibomian gland dysfunction and dry eye disease. Thode, et al., Drugs 75(11):177-85 (July 2015);

E) ratite oils (ostrich, rhea and emu) and tea tree oil are reported to reduce blood mononuclear cell viability and inhibit IFNy and appear to reduce keratinocyte cell growth and cell proliferation, and promote would healing. Bennett et al., Pout. Sci. 94(9): 2288-96 (September 2015);

F) Antioxidant, anti-inflammatory, antimicrobial and antiviral activities of oleuropein. Syed Haris Omar, Sci. Pharm. 78(2):133-154 (April-June 2010).

The testing (or assessment) is preferably conducted by or under the supervision of a medical professional, e.g., a physician, optometrist, ophthalmic technician, nurse, nurse practitioner, physician's assistant or other medical professional or a comparably trained person.

The testing may advantageously include one or more tests to determine if the patient has dry eye syndrome, the characteristics of dry eye syndrome present in the patient under examination, and, how severe or serious the syndrome in the patient is. Such treating can also identify one or more treatment compositions, e.g., balms, emulsions or artificial tear formulations, that may be appropriate for treating the patient under examination.

The testing may include at least one determination, and preferably a plurality of determinations, regarding the amount and/or quality of the tears in the patient's eye or eyes and the effect of these tears on the patient's eye. For example, tests can be conducted to determine one or more, or two or more, or three or more, of the viscosity, pH, tonicity and/or osmolality, protein (e.g., mucin) content, refractive index, surface tension, specific gravity, and other property or properties of the tears in the patient's eyes. Such testing may include corneal staining, determination of tear breakup time, determination of the degree of conjunctival redness, and Schirmer's test, and one or more other test to help determine the amount and properties of the patient's tears. In addition, the testing preferably includes a visual evaluation of the patient's eyes to make a qualitative evaluation of the extent or seriousness (severity) of the dry eye syndrome in the patient's eyes.

Inquiring of the patient, e.g., through the use of an interview and/or a check list filled out by the patient, as to symptoms of DES, such as what degree, if any, of sensitivity and/or other conditions and/or issues the patient has that might affect the course of treatment of the patient's dry eye syndrome, and the suitability, or lack thereof, of any artificial tear products used in the past by the patient. For example, and without limitation, the patient may be asked about the presence of allergies, past sensitivity to having eye drops in the patient's eyes, adverse drug reactions, for example, any adverse reactions to one or more of the components of the composition or compositions that are being contemplated for use in treating the patient's DES.

The results of the testing and inquiring are preferably considered by a medical professional as part of a treatment plan. Based on the testing and inquiring, a treatment composition is provided for use in the patient's eye to treat the patient's DES.

This treatment composition is selected from a series or plurality of different topical ophthalmic compositions based on refractive index, clarity, surface tension, specific gravity, pH, tonicity and/or osmolality, protein (e.g., mucin) content and any other property or properties of the tears in the patient's eyes. In other words, the state of the patient's dry eye syndrome and the individual or specific sensitivities, conditions and/or other issues of the patient which may affect the treatment of the patient's eye, for example, sensitivity to certain eye drops or medication in the patient's eye, are considered, and form at least a significant part or even substantially the entire basis for providing a specific treatment composition from among a plurality of treatment compositions to treat the patient's DES.

In one example of the present invention, a treatment composition for treating an eye of a human comprises water and one or more hydrophobic component selected from the group consisting of jojoba oil, derivatives of jojoba oil, avocado oil, derivatives of avocado oil, olive oil, and mixtures thereof and castor oil, and derivatives thereof, the hydrophobic component being present in an amount effective to beneficially treat dry eye syndrome when placed in an eye of a human afflicted with dry eye syndrome.

Such a composition is highly effective in treating dry eye syndrome. Importantly, it has been found that a series of relatively few such compositions are effective to treat a wide range of human patients who have DES in widely varying severities and who have a wide range of other issues, such as issues regarding comfort, and thus patient compliance with the treatment regimen, which may affect the treatment of dry eye syndrome.

In other words, it has been found that a suite or series of about 4 or about 5, or about 6, or about 7, or about 8, or about 9, or about 10, different topical ophthalmic artificial tear treatment compositions can be formulated in accordance with the present invention at least one of which will effectively and comfortably treat about 90% or about 95% or about 98% of the patients suffering from dry eye syndrome.

In certain formulations comprising high molecular weight polyacrylic acid polymers (referred to herein and sold under the trade names Carbopol® Noveon® and Pemulen®; but by these names also mean to include (unless specifically indicated otherwise) the same or similar compounds sold under other trade names as generic emulsion stabilizers), it has unexpectedly been found that making dry eye treatment formulations containing from about 0.1% (w/v) to about 0.5% of a natural oil requires about 10-fold less Pemulen® than might otherwise be expected in a dry eye treatment formulation, such as an eye drop, an eye emulsion, such as an eye or eye lid emulsion.

Each of the different compositions of the series of compositions has a different combination of components, for example, different components and/or different concentrations of the same components, from composition to composition. The different combinations of components present in the compositions are provided depending on the severity of a patient's dry eye syndrome and the presence of sensitivity and/or discomfort and/or one or more other issues the patient has, for example, with regard to the patient having eye drops in the patient's eye.

One or more or all of the series of treatment compositions may be substantially steroid free. By "substantially steroid free" is meant steroid free, or having an amount of a steroid having no discernable therapeutic effect on dry eye disease. In another example, one or more or all of the compositions may include a useful or effective amount of a steroid. In some examples, the treatment compositions may lack any additional therapeutic component (any drug regulated by the U.S. Food and Drug Administration). In other examples, the treatment compositions of the present invention may comprise one or more therapeutic composition.

In one example, one or more or all of the series of compositions may include a cyclosporin, for example, cyclosporin A, in an amount effective to at least aid in treating dry eye syndrome in a patient to whom the composition is administered. One or more or all of the compositions in a series of compositions may be substantially free of cyclosporin. By "substantially cyclosporin free" is meant cyclosporin free, or having an amount of a cyclosporin having no discernable therapeutic effect on dry eye disease. The amount, if any, of cyclosporin, for example, cyclosporin A, present in at least one of the present compositions, may in certain examples be in a range, by weight, of about 0.05% to about 2.0%, or about 0.05% to about 1.5%, or about 0.1% to about 1.0%, or about 0.2% to about 1%.

As noted above, one or more of the compositions may include an amount of jojoba oil component, meaning to include jojoba oil (liquid jojoba wax), jojoba oil derivatives, e.g., hydrophobic jojoba oil derivatives, and mixtures of two or more thereof. The jojoba oil component may be present, either as the sole oil, or in combination with one or more additional oil, in one or more or all of the series of compositions in a range of about 0.05% (w/v) to about 1.0% (w/v), or about 0.1% % (w/v) to about 0.75% % (w/v) or about 0.1% % (w/v) to about 0.5% (w/v), or about 0.1%, % (w/v) to about 0.25% (w/v). If present, the concentration of jojoba oil component may vary or be the same in each composition of the series of compositions. One or more of these compositions may be free of jojoba oil component.

As noted above, one or more of the compositions may include an amount of avocado oil component, meaning to include avocado oil, avocado oil derivatives, e.g., hydrophobic avocado oil derivatives, and mixtures of two or more thereof. The avocado oil component may be present, either as the sole oil, or in combination with one or more additional oil, in one or more or all of the series of compositions in a range of about 0.05% (w/v) to about 1.0% (w/v), or about 0.1% % (w/v) to about 0.75% % (w/v) or about 0.1% % (w/v) to about 0.5% (w/v), or about 0.1% % (w/v) to about 0.25% (w/v). If present, the concentration of avocado oil component may vary or be the same in each composition of the series of compositions. One or more of these compositions may be free of avocado oil component.

As noted above, one or more of the compositions may include an amount of tea tree oil component, meaning to include tea tree oil, tea tree oil derivatives, e.g., hydrophobic tea tree oil derivatives, and mixtures of two or more thereof. The tea tree oil component may be present, either as the sole oil, or in combination with one or more additional oil, in one or more or all of the series of compositions in a range of about 0.05% (w/v) to about 1.0% (w/v), or about 0.1% % (w/v) to about 0.75% % (w/v) or about 0.1% % (w/v) to about 0.5% (w/v), or about 0.1% % (w/v) to about 0.25% (w/v). If present, the concentration of tea tree oil component may vary or be the same in each composition of the series of compositions. One or more of these compositions may be free of tea tree oil component.

As noted above, one or more of the compositions may include an amount of argan oil component, meaning to include argan oil, argan oil derivatives, e.g., hydrophobic argan oil derivatives, and mixtures of two or more thereof. The argan oil component may be present, either as the sole oil, or in combination with one or more additional oil, in one or more or all of the series of compositions in a range of about 0.05% (w/v) to about 1.0% (w/v), or about 0.1% % (w/v) to about 0.75% % (w/v) or about 0.1% % (w/v) to about 0.5% (w/v), or about 0.1% % (w/v) to about 0.25% (w/v). If present, the concentration of argan oil component may vary or be the same in each composition of the series of compositions. One or more of these compositions may be free of argan oil component.

As noted above, one or more of the compositions may include an amount of oleuropein component, meaning to include oleuropein, oleuropein derivatives, e.g., hydrophobic oleuropein derivatives, and mixtures of two or more thereof. The oleuropein component may be present, either as the sole oil, or in combination with one or more additional oil, in one or more or all of the series of compositions in a range of about 0.05% (w/v) to about 1.0% (w/v), or about 0.1% % (w/v) to about 0.75% % (w/v) or about 0.1% % (w/v) to about 0.5% (w/v), or about 0.1% % (w/v) to about 0.25% (w/v). If present, the concentration of oleuropein component may vary or be the same in each composition of the series of compositions. One or more of these compositions may be free of oleuropein component.

As noted above, one or more of the compositions may include an amount of castor oil, meaning to include castor oil derivatives, e.g., hydrophobic castor oil derivatives, and mixtures of two or more thereof. The castor oil component may be present, either as the sole oil, or in combination with one or more additional oil, in one or more or all of the series of compositions in a range of about 0.05% (w/v) to about 1.0% (w/v), or about 0.1% % (w/v) to about 0.75% % (w/v) or about 0.1% (w/v) to about 0.5% (w/v), or about 0.1% % (w/v) to about 0.25% (w/v). If present, the concentration of castor oil component may vary or be the same in each composition of the series of compositions. One or more of these compositions may be free of castor oil component.

Generally speaking, natural tears have a pH of about 7.4, but can tolerate slightly acidic pH values. While tonicity and osmolanty are often confused, tonicity is the measure of the osmotic pressure gradient between two solutions, and is thus only influenced by solutes that cannot cross a semipermeable membrane, since these are the only solutes influencing the osmotic pressure gradient at equilibrium. The osmolarity of natural tears is about 290 mOsm (corresponding to about 0.9% (w/v) sodium chloride solution; the outer cornea can tolerate solutions equivalent to a range of from about 0.5% to about 1.8% sodium chloride (w/v)). In some cases of dry eye syndrome, the tear fluid can be hypertonic, and a hypotonic tear hyperosmolarity exists and may require remediation when the osmolarity is equal to or greater than about 340 mOsm/l. A hypo-osmolalar treatment composition (e.g., less than about 300 mOsmol/L) may be used to counteract this condition.

Since the artificial tear compositions do not, in preferred embodiments, contain protein, a viscosity-enhancing component may be added when the viscosity normally provided by mucin is required. An advantage of added viscosity-enhancing components is that the artificial tear treatment composition may remain on the surface of the cornea for a longer time period than it would without the viscosity-enhancing component. The viscosity of the treatment composition may range from about 1.0 to about 100 cP; preferably from greater than 1 cP to about 60 cP; more preferably from about 1.1 cP to about 55 cP; more preferably from about 1.2 cP to about 50 cP. In certain examples the treatment composition may comprise eye drops or artificial tears having a viscosity of between about 1 cP and about 3 cP. Low viscosity is less than about 15 cP, whereas high viscosity is greater than or equal to about 15 cP. Normal surface tension is greater than about 40 dynes/cm. Low surface tension is less than or equal to about 40 dynes/cm.

The treatment compositions may include an amount of at least one additional component effective to provide a benefit to the patient to whom the treatment composition is provided. In such examples, any ophthalmically acceptable component may be included in one or more of the present compositions to provide a desired benefit to the composition(s) and/or to the patient.

For example, the treatment composition may comprise one or more organic or inorganic solute as a tonicity agent (such as sodium or potassium salts of chloride, hyaluronate, acrylate, glycerin and the like); buffers, such as metal salts of borate or phosphate, to maintain the pH within physiologically acceptable ranges; viscosity enhancers (such as, without limitation, methylcellulose (MC), hydroxypropyl methylcellulose (HPMC), hydroxyethyl cellulose (HEC), Carbopol®, Pemulen®, Noveon®, polyvinyl alcohol, polyethylene glycol, polyoxyethylene polyoxypropylene glycol (PEPPG), hyaluronic acid salts such as sodium hyaluronate, and polyvinyl pyrrolidone); surfactants, such as a polyoxyethylene sorbitan esters and their derivatives (for example Polysorbate® 80), polyoxyl 40 stearate, polyoxyl 40 hydrogenated castor oil, mixtures thereof, and the like. Some of these agents may have more than one function in the treatment compositions of the present application, for example, all solutes contribute to the total tonicity of a liquid, and agents such as CMC, HPMC, Pemulen® and Carbopol® are viscosity enhancing agents, but may also function as emulsion stabilizers.

In certain examples, the treatment compositions of the present invention may contain a biocidal agent as a preservative such as benzalkonium chloride (BAK), benzethonium chloride, or another quaternary ammonium preservative, methyl and ethyl parabens, phenylmercuric salts such as phenylmercuric acetate and phenylmercuric nitrate, sodium perborate, chlorobutanol, hexetidine, stabilized oxychoro complex (Purite®), and stabilized thimerosal. However, in other examples the treatment compositions of the present invention may be preservative-free formulations available, for example, as sterile unit doses or sterile multidose formulations with applicators designed to maintain sterility as far as possible.

Research has demonstrated that even on the low concentrations traditionally used, biocides may be cytotoxic to corneal cells upon repeated use. Thus, BAK, which is the most commonly used biocide in ophthalmic preparations, can lead to corneal epithelial separation, at the concentrations used (ranging from about 0.004% to about 0.02% (w/v)). While effective against some viruses, fungi and protozoa, it is not effective against all potential contaminants, most notably strains of *Pseudomonas aeruginosa*. A chelating agent such as EDTA (ethylenediamine tetracetic acid) can be added to overcome the resistance of *P. aerugenosa*, but EDTA is itself harmful to corneal tissue. Other biocides, such as Purite® or perchlorate are much less harmful to ocular tissues, but may have less effective biocidal activity.

Therefore in some examples of the present invention, it is desirable to add a hydrophobic component comprising one or more natural oil or similar substance (all of which will be called "oils" herein), such as (without limitation) jojoba oil, avocado oil, tea tree oil, coconut oil, argan, oleuropein, cottonseed oil, sunflower oil, maize oil, linseed oil, rapeseed oil, tea tree oil, argan oil, castor oil, soybean oil, caraway oil, rosemary oil, peppermint oil, sunflower oil, *Eucalyptus* oil, bergamot oil, fennel oil, sesame oil, menthol oil, *Ginseng* oil, jujube oil, okra oil; oils (other than those listed above) suitable for ophthalmic use containing terpenoids, or olive oil, as a secondary biocide having biocidal or antimicrobial activity. Such agents may permit a reduction of the concentration of the primary biocide and/or chelating agent (such as the combination of BAK and EDTA).

In other examples the treatment compositions of the present invention may be provided as an unpreserved composition in sterile unit dosage forms.

In still other examples of the invention, the treatment compositions disclosed herein may provide a carrier or vehicle formulation for the inclusion of active therapeutic agents for topical delivery to the eye. For example, there are a number of drugs that may have novel effects when formulated in the present formulations due to one or more of a number of characteristics including the unique interaction of the preferred oils or liquid waxes with the drug moiety, the novel ocular comfort characteristics of these formulations, and the advantageous drug delivery platform provided by the formulations.

Such drugs may include, without limitation, anti-inflammatory drugs, particularly where such formulations (for example, with oils and/or waxes having their own anti-inflammatory activities) may augment the anti-inflammatory effect and/or improve delivery and tolerability of the drug. Beneficial anti-inflammatory agents: methotrexate; lifitegrast; non-steroidal anti-inflammatory drugs such as diclofenac sodium, flubiprofen sodium, ketorolac tromethanimne, bromfenac, and aprafenac; anti-allergy drugs such as ketotifen, azalastine, epinastine, olapatadine, and alcaftidine; corticosteroids like difluprednate, prednisolone acetate, loteprednol, fluorometholone, and dexamethasone; calcineurin inhibitors such as tacrolimus and cyclosporine; and other anti-inflammatory drugs like methotrexate and rapamycin.

The present formulations can also be useful in formulating large molecule protein biologic agents where the oil emulsion could improve protein stabilization. This would be particularly novel considering oils can cause aggregation i.e. protein instability. The oils we are using are unique for the eye, and are useful at lower concentrations than prior formulations. The oils, together with the other ingredients, have a surprisingly stabilizing impact. This can be used to improve absorption and delivery of proteins such as infliximab, adalimumab, etanercept, bevacizumab, ranabizumab, and aflibercept.

Additionally, the soothing properties of the present formulation may be advantageously be utilized to counteract irritation reported as being properties of some topical ocular therapeutic agents. For example such formulations, with or without preservatives, may be used in the formulation of drugs such as brimonidine, brinzolamide, pilocarpine, travaprost, latanoprost, bimatoprost, tafluprost, povidone iodine, and silver nitrate.

Other specific examples of oils which may be used alone, or in combination with other oils, in the treatment compositions of the present invention include avocado oil cottonseed oil, sunflower oil, maize oil, linseed oil, rapeseed oil, tea tree oil, argan oil, castor oil, soybean oil, caraway oil, rosemary oil, peppermint oil, sunflower oil, *Eucalyptus* oil, bergamot oil, fennel oil, sesame oil, *Ginseng* oil, jujube oil, okra oil and/or one or more other oils, e.g., natural oils, having an antimicrobial effect when placed in the patient's eye.

The treatment composition may be provided in any suitable form, for example, in the form of a solution, a mixture, an emulsion or a microemulsion.

In one example, the invention is directed to testing a patient for the presence of the signs and symptoms of DES, such as through testing the tears of the patient, interviewing the patient, selecting a suitable artificial tear treatment composition from among a suite of, e.g., 4 to 7, different treatment compositions, and providing the patient with a suitable artificial tear, balm or emulsion treatment composition selected at least in part of the results of the testing and assessment.

Testable tear properties include refractive index (RI), surface tension (ST), specific gravity (SG), viscosity, protein content, lipid concentration, osmolality tear breakup time and tonicity. DES can also be assessed by examining the patient by measuring clinical signs and patient symptoms including corneal staining, conjunctival hyperemia, conjunctival staining, tear production, tear break-up time, and symptom severity including pain, discomfort, vision blurring, and the Ocular Surface Disease Index (OSDI). Additionally, eyelid inflammation can be assessed and scored. These parameters can be compared to normal values and used in the preparation of the treatment compositions of the present invention.

There is substantial patient to patient variability in the severity and character of DES. Individual patients may benefit from different treatment and tear replacement therapy. Significantly, the present inventors have found that Clarity ("C"; Percent Transmittance at 580 nm) and SG can be utilized to characterize the composition of topical ophthalmic formulations from a therapeutic potential. Refractive index of an artificial tear should preferably be similar to the refractive index of the normal tear film: e.g., about 1.337. In addition to the long-term therapeutic effect of tear replacement therapy to the ocular surface one must consider the adverse effect of tear formulations on vision. These values, determined using a spectrophotometer, a refractometer and pycnometer, have contributed to a novel way to characterize both the ocular surface healing effects and the visual obscuration potential of such formulations since they capture the contributions from all ingredients including oil-containing preparations and RI can help define optical clarity of a preparation. By using techniques such as refractive index matching of multiphase preparations or the preparation of microemulsions to obtain optical clarity this approach can help minimize visual blurring upon installation of the treatment composition and/or provide the patient with their most preferred "optically customized" product.

It will be understood that while increased viscosity of a tear formulation may increase its healing potential, such increased viscosity may simultaneously decrease the patient's ability to tolerate the composition.

Understanding this relationship allows the inventors to select a range of formulations with different properties matched to individual patient disease criteria while minimizing the impact of each formulation on vision.

In some cases if, following the providing step, the treatment composition proves ineffective and/or unsatisfactory as a treatment for the patient's dry eye syndrome, the providing step may be refined by reassessing the patient specific parameters and using a different one of the suite or series of different treatment compositions being provided. This may be repeated, if necessary, until a composition is provided to the patient that is the most effective and satisfactory artificial tear treatment composition available from among the suite of treatment compositions for the patient's dry eye syndrome.

In one embodiment of the present method, two or more of the compositions can be used sequentially to address the patient's dry eye syndrome. For example, during a period of time during the day the patient's eyes may be exposed to harsh conditions which require using a dry eye treatment composition to mitigate against these harsh conditions so as to effectively control the relatively severe dry eye syndrome in the patient's eyes caused thereby. During less stressful times, for example, during the evening and/or in preparation for sleep, the dry eye syndrome may be less severe. The dry eye syndrome experienced by a patient at these times may be substantially more mild. At these times, a more mild artificial tear treatment composition may be employed to mitigate the patient's dry eye syndrome while being more comfortable for the patient to use so that the dry eye syndrome can be healed.

Putting it more broadly, different artificial tear treatment compositions selected from the suite of from about 4 to about 10 artificial tear treatment compositions may be employed when the eye or eyes are subjected to different conditions. The flexibility of being able to use more than one treatment composition depends, for example, on the environment to which the eye is exposed and allows the patient to effectively control the dry eye syndrome he or she is experiencing regardless of changing conditions to which the eyes may be exposed and the severity of the dry eye syndrome in the patient's eyes.

Preferably, the hydrophobic component comprises one or more natural plant-based oils, hydrophobic derivatives thereof and the like. Examples of useful oil materials include, without limitation, plant-based oils, animal oils, mineral oils, synthetic oils and the like and mixtures thereof. The hydrophobic component may comprise one or more higher fatty acid glycerides. Very preferably at least one oil is selected from a plant-based oil. Excellent results are obtained when the hydrophobic component is selected from the group consisting of jojoba oil, hydrophobic derivatives of jojoba oil, castor oil, hydrophobic derivatives of castor oil, avocado oil, hydrophobic derivatives of avocado oil and mixtures thereof. Very preferred embodiments of the present invention comprise avocado oil. Other preferred embodiments comprise castor oil and at least one additional oil—most preferably the additional oil is of vegetal origin.

Components may be employed in the treatment compositions of the present invention, which are effective to perform two or more functions in the presently useful compositions. For example, as indicated above, carboxymethylcellulose (CMC), HPMC, Pemulen® and Carbopol® are viscosity enhancing agents, but may also function as emulsion stabilizers. For example, components that are effective as both emulsifiers and surfactants may be employed, and/or components that are effective as both polyelectrolyte components and viscosity inducing components may be employed. The specific treatment composition chosen for use in the treatment of a given patient in the present invention advantageously is selected taking into account various factors present in the specific application at hand, for example, the desired treatment of the patient's dry eye syndrome to be achieved, the desired properties of the compositions to be employed, for example, taking into account the sensitivities of the patient to whom the composition is to be administered, and similar factors.

In certain examples, the therapeutic compositions of the present invention may be useful either by themselves as, or as a base for, skin treatments, such as moisturizers or cosmetics for use near the eye. Unlike cosmetics such as common eye shadow or eyeliner, the present compositions are lubricating to the eye, and thus skin treatments, and cosmetics made using such compositions result in reduced ocular irritation in the event that the cosmetic inadvertently gets into the eye. This may be of particular benefit when a patient has a coexisting dry eye disease, since ingredients applied to the eyelid can penetrate the eyelid to reach the eye.

Additionally, the present compositions may be useful for the treatment of the exterior of the eyelid, as a moisturizing skin aid, which, unlike other products, does not clog the pores or glands. Such compositions may also contain anti-bacterial components to the treatment or prevention of infection, such as blepharitis.

The presently useful compositions advantageously are ophthalmically acceptable. Each of the components or materials in the presently useful compositions preferably is ophthalmically acceptable in the concentration used in the presently useful compositions. A composition, component or material is ophthalmically acceptable when it is compatible with ocular tissue, that is, it does not cause significant or undue detrimental effects when brought into contact with ocular tissues.

Such compositions have a pH within the range of about 6 to about 10, preferably in a range of about 7.0 to about 8.0 and more preferably in a range of about 7.2 to about 7.6, or about 7.4, or so.

The present methods preferably provide for an administering step comprising topically administering one of the presently useful compositions to the corneal surface of the eye or eyes of a human patient. Administration can range from instillation, to use of a cotton swab or finger.

Each and every feature described herein, and each and every combination of two or more of such features, is included within the scope of the present invention provided that the features included in such a combination are not mutually inconsistent.

The presently useful compositions may include one or more other components in amounts effective to facilitate the usefulness and effectiveness of the present methods and/or the presently useful compositions. Examples of such one or more other components include, without limitation, emulsifier components, surfactant components, tonicity components, poly electrolyte components, emulsion stability components, viscosity inducing components, demulcent components, anti-oxidant components, acid and/or bases to adjust the pH of the composition, buffer components, preservative components and the like. A list of ophthalmic inactive ingredients can be found at the U.S. Food and Drug Administration website at the cder Inactive Ingredient database, accessible at the link https://www.fda.gov/media/72482/download. This list of inactive ingredients is hereby incorporated by reference herein.

In one embodiment, the presently useful compositions are substantially free of preservatives. Thus, the presently useful compositions may be sterilized and maintained in a sterile condition prior to use, for example, provided in a sealed package or otherwise maintained in a substantially sterile condition.

Any suitable emulsifier component may be employed in the presently useful compositions, provided, that such emulsifier component is effective in forming and/or maintaining an emulsion or microemulsion, while having no significant or undue detrimental effect or effects on the compositions during storage or use.

In addition, the presently useful compositions, as well as each of the components of the present compositions in the concentration present in the composition advantageously are ophthalmically acceptable.

Useful emulsifier components may be selected from such component that are conventionally used and well known in the art. Examples of such emulsifier components include, without limitation, surface-active components or surfactant components, which may be anionic, cationic, nonionic or amphoteric in nature. In general, the emulsifier component includes a hydrophobic constituent and a hydrophilic constituent. Advantageously, the emulsifier component is water soluble in the presently useful compositions. Preferably, the emulsifier component is nonionic. Specific examples of suitable emulsifier components include, without limitation, Polysorbate® 80, polyoxyalkylene alkylene ethers, polyalkylene oxide ethers of alkyl alcohols, polyalkylene oxide ethers of alkylphenols, other emulsifiers/surfactants, preferably nonionic emulsifiers/surfactants, useful in ophthalmic compositions, and the like and mixtures thereof.

The emulsifier component is present in an amount effective in forming an emulsion and/or in maintaining the hydrophobic component in emulsion with the water or aqueous component. In one preferred embodiment, the emulsifier component is present in a weight percentage range of about 0.01% to about 5%, more preferably about 0.02% to about 2% and still more preferably about 0.05% to about 1.5% by weight of the presently useful compositions. Preferably surfactant component(s), if present, is/are non-ionic and only present in a sufficient concentration to emulsify the hydrophilic and hydrophobic phases.

Polyelectrolyte or emulsion stabilizing components may be included in the presently useful compositions. Such components may be effective in maintaining the electrolyte balance in the presently useful emulsions, thereby stabilizing the emulsions and preventing the emulsions from breaking down prior to use. In one embodiment, the presently useful compositions include a polyanionic component effective as an emulsion stabilizing component. Examples of suitable polyanionic components useful in the presently useful compositions include, without limitation, anionic cellulose derivatives, anionic acrylic acid-containing polymers, anionic methacrylic acid-containing polymers, anionic amino acid-containing polymers and the like and mixtures thereof.

One useful class of polyanionic components includes one or more polymeric materials having multiple anionic charges. Examples include, but are not limited to:
- metal carboxy methylcelluloses
- metal carboxy alkyl methylcelluloses
- metal carboxymethyl hydroxyethylcelluloses
- metal carboxymethyl starches
- metal carboxymethyl hydroxyethyl starches
- hydrolyzed polyacrylamides and polyacrylonitrile heparins
- glucoaminoglycans
- hyaluronic acid
- chondroitin sulfate
- dermatan sulfate
- peptides and polypeptides
- alginic acid
- metal alginates
- homopolymers and copolymers of one or more of:
- acrylic and methacrylic acids
- metal acrylates and methacrylates
- vinylsulfonic acid
- metal vinylsulfonate
- amino acids, such as aspartic acid, glutamic acid and the like
- metal salts of amino acids
- p-styrenesulfonic acid
- metal p-styrenesulfonate
- 2-methacryloyl oxyethyl sulfonic acids
- metal 2-methacryloyl oxyethyl sulfonates
- 3-methacryloyloxy-2-hydroxypropyl sulfonic acids
- metal 3-methacryloyloxy-2-hydroxypropyl sulfonates
- 2-acrylamido-2-methylpropane sulfonic acids
- metal 2-acrylamido-2-methylpropane sulfonates
- allylsulfonic acid
- metal allylsulfonate and the like.

One particularly useful emulsion stabilizing component includes crosslinked polyacrylates, such as carbomers and Pemulen® materials. Pemulen® is a registered trademark of B.F. Goodrich for polymeric emulsifiers. Pemulen® materials include acrylate/C10-30 alkyl acrylate cross-polymers, or high molecular weight co-polymers of acrylic acid and a long chain alkyl methacrylate cross-linked with allyl ethers of pentaerythritol. Carbomers include polyacrylate polymers of various molecular weights.

The presently useful polyanionic components may also be used to provide a suitable viscosity to the presently useful compositions. Thus, the polyanionic components may be useful in stabilizing the presently useful emulsions and in providing a suitable degree of viscosity to the presently useful compositions.

The polyelectrolyte or emulsion-stabilizing component may advantageously be present in an amount effective to at least assist in stabilizing compositions in the form of emulsions. For example, a polyelectrolyte/emulsion stabilizing component may be present in an amount in a range of about 0.01% by weight or less to about 1% by weight or more, preferably about 0.02% by weight to about 0.5% by weight, of the composition. Applicants have discovered that in certain emulsion stabilizing components such as Pemulen®, may be used at surprisingly low concentrations, such as below 0.2% (w) or below 0.1% by weight to provide a suitably high viscosity to the therapeutic composition.

Solubilizing surfactant agents suitable for over-the-counter topical ophthalmic use may include Polysorbate® 80, polyoxyethylene hydrogenated castor oil 60 (also known as PEG 60 hydrogenated castor oil), tyloxapol, polyethyleneglycol monostearates, as well as PEG 40 hydrogenated castor oil, and acrylates/C10-30 alkyl acrylate crosspolymer (e.g., Pemulen®).

Any suitable tonicity component may be employed in accordance with the present invention. Organic or inorganic tonicity components may be employed. Useful organic tonicity components or agents include, without limitation, glycerin, mannitol, sorbitol and the like and mixtures thereof. Useful inorganic tonicity components may include salts such as alkali metal salts of anions such as citrate, chlorate, borate, phosphate, and hyaluronate. The presently useful compositions, for example, emulsions or microemulsions, may preferably be within the range of plus or minus about 20% or about 10% from being isotonic; however in other examples one or more of the suite of treatment compositions may be hypotonic or hypertonic, respectively, in order to restore a patient's hypertonic or hypotonic tears to an essentially isotonic condition in situ.

Thus, the tonicity of one or more compositions in the plurality of compositions may be varied to facilitate the one or more compositions being useful for a particular group or class of patents.

Ophthalmic demulcent components may be included in effective amounts in the presently useful compositions. For example, ophthalmic demulcent components such as carboxymethylcellulose, other cellulose polymers, dextran 70, gelatin, glycerine, polyethylene glycols (e.g., PEC; 300 and PEG 400), Polysorbate® 80, propylene glycol, polyvinyl alcohol, povidone and the like and mixtures thereof, may be used in the present ophthalmic compositions useful for treating dry eye.

The demulcent components are preferably present in the therapeutic compositions, for example, the artificial tear compositions, in an amount effective in enhancing the lubricity of the presently useful compositions. The amount of demulcent component in the present compositions may be in a range of at least about 0.01% or about 0.02% to about 0.5% or about 1.0% by weight of the composition, depending in part on the specific demulcent (or combinations of demulcents) used.

Many of the presently useful polyelectrolyte/emulsion stabilizing components may also be effective as demulcent components, and vice versa. The emulsifier/surfactant components may also be effective as demulcent components and vice versa.

The presently useful compositions may include an effective amount of a preservative component. Any suitable preservative or combination of preservatives may be employed. Examples of suitable preservatives include, without limitation, benzalkonium chloride (BAK), benzethonium chloride, or another quaternary ammonium preservative, methyl and ethyl parabens, phenylmercuric salts such as phenylmercuric acetate and phenylmercuric nitrate, perborate salts, chlorobutanol, hexetidine, perchlorate salts, stabilized oxychoro complex (Purite®), stabilized thimerosal and the like and mixtures thereof. The amounts of preservative components included in the present compositions are effective in preserving the compositions and can vary based on the specific preservative component employed, the specific composition involved, the specific application involved, and the like factors. Preservative concentrations are often in the range of about 0.00001% to about 0.05% or about 0.1% (w/v) of the composition, although other concentrations of certain preservatives may be employed. Generally it is desirable to utilize the lowest concentration of a preservative (or mixture of preservatives) able to provide the necessary preservative efficacy, since many preservatives may be cytotoxic at higher concentrations. Chlorine and boron-based preservatives may be less cytotoxic than BAK and other quaternary ammonium salts.

Very useful examples of preservative components in the present invention include, but are not limited to, chlorite components. Specific examples of chlorite components useful as preservatives in accordance with the present invention include stabilized chlorine dioxide (SCD), metal chlorites such as alkali metal and alkaline earth metal chlorites, and the like and mixtures thereof. Technical grade (or USP grade) sodium chlorite is a very useful preservative component. The exact chemical composition of many chlorite components, for example, SCD, is not completely understood. The manufacture or production of certain chlorite components is described in McNicholas U.S. Pat. No. 3,278,447, which is incorporated in its entirety by reference herein. Specific examples of useful SCD products include that sold under the trademark Dura Klor® by Rio Linda Chemical Company, Inc., and that sold under the trademark Anthium Dioxide® by International Dioxide, Inc. An especially useful SCD is a product sold under the trademark Bio-Cide® by Bio-Cide International, Inc., as well as a product identified by Allergan, Inc. by the trademark Purite®.

Other useful preservatives include antimicrobial peptides. Among the antimicrobial peptides which may be employed include, without limitation, defensins, peptides related to defensins, cecropins, peptides related to cecropins, magainins and peptides related to magainins and other amino acid polymers with antibacterial, antifungal and/or antiviral activities. Mixtures of antimicrobial peptides or mixtures of antimicrobial peptides with other preservatives are also included within the scope of the present invention.

Antimicrobial activity(ies) may also be inherent as a biological activity of one or more oil, wax or other hydrophobic component of the composition, or may be comprised in an agent included particularly for this purpose. In such cases it may be possible to consider the hydrophobic component as a secondary preservative or antimicrobial, and therefore to reduce the concentration (and the possibility of adverse cytotoxic effects) of the primary antimicrobial or preservative.

Additionally or alternatively, in some examples it is very desirable to include components having an anti-inflammatory activity in the present compositions. Such anti-inflammatory activity(ies) may be inherent as a biological activity of one or more oil, wax or other hydrophobic component of the composition, or may be comprised in an agent included particularly for this purpose.

The present compositions may in some examples be provided as preservative-free compositions, for example, in sterile, single use containers. In other examples the type and/or amount, if any of preservatives may be different in the series of compositions. Such flexibility in the make-up of the series of compositions may be useful in selecting the correct or best treatment composition for an individual patient.

The compositions of the present invention may include viscosity modifying agents or components, such as cellulose polymers, including hydroxypropyl methyl cellulose (HPMC), hydroxyethyl cellulose (HEC), ethyl hydroxyethyl cellulose, hydroxypropyl cellulose, methyl cellulose and carboxymethyl cellulose; carbomers (e.g. Carbopol®, and the like); polyvinyl alcohol; polyvinyl pyrrolidone; alginates; carrageenans; and guar, karaya, agarose, locust bean, tragacanth and xanthan gums. Such viscosity modifying components are employed, if at all, in an amount effective to provide a desired viscosity to the present compositions. The concentration of such viscosity modifiers will typically vary between about 0.01% to about 5% w/v of the total composition, although other concentrations of certain viscosity modifying components may be employed.

The presently useful compositions may be produced using conventional and well known methods useful in producing ophthalmic products, for example, solutions, oil-in-water emulsions and the like.

In one example, the oily phase of the emulsion can be combined with any other hydrophobic components in the oily material phase. The oily phase and the water may be separately heated to an appropriate temperature. This temperature may be the same in both cases, generally a few degrees to about 10° C. above the melting temperature of the ingredient(s) having the highest melting point in the case of a solid or semi-solid oily phase for emulsifier components in the oily phase. Where the oily phase is a liquid at room temperature, a suitable temperature for preparation of a composition may be determined by routine experimentation in which the melting point of the ingredients aside from the oily phase is determined. In cases where all components of either the oily phase or the water phase are soluble at room temperature, no heating may be necessary. Non-emulsifying agents which are water-soluble are dissolved in the water and oil-soluble components including the surfactant components are dissolved in the oily phase.

In one example, an oil-in-water emulsion is created as follows: the final oil phase is gently mixed into either an intermediate phase, preferably de-ionized water, or into the final aqueous phase to create a suitable dispersion and the product is allowed to cool with or without stirring. In the case where the final oil phase is first gently mixed into an intermediate water phase, the resulting emulsion concentrate is thereafter mixed in the appropriate ratio with the final aqueous phase. In such cases, the emulsion concentrate and the final aqueous phase may not be at the same temperature or heated above room temperature, as the emulsion may be already formed at this point.

Stable emulsions are formed and dispersed by the application of energy to a mixture of immiscible fluids. A "stable" emulsion is meant to refer to an emulsion in which the hydrophobic and hydrophilic phases do not substantially separate within a length of time, such 30 days, or more preferably 60 days, or more preferably 90 days, or more preferably 6 months, or more preferably a year or more.

Gentle mixing, as described above, involves the application of relatively low amounts of energy. This can be advantageous when using materials having a relatively high molecular weight (MW), as gentle mixing generates comparatively few and relatively weak shear forces to cause break these large MW molecules.

Depending upon a number of factors, including the viscosity of the components of the emulsion and of the resulting emulsion as it is formed, and the chemical and physical characteristics of these components (including, in addition to viscosity: molecular weight, polarity, charge, hydrophobicity/hydrophilicity/amphophilicity, etc.), a greater amount of energy may be required to form a stable emulsion in which all the components remain homogeneously dispersed in a stable emulsion.

High energy methods include high-energy, high-shear mixing (e.g., using a Silverston mixer), microfluidization (application of high pressure to generate high shear forces) and ultrasonication methods. These methods can be used to reduce globule size in an emulsion (i.e., oil droplet size in an oil in water emulsion), and to ensure homogeneous dispersion of ingredients in the emulsion. The high shear forces may also cause shearing of macromolecules and high molecular weight polymers such as Pemulen® and some celluloses and cellulose derivatives, thereby decreasing their viscosity.

The oil-in-water emulsions of the present invention can be sterilized after preparation using heat, for example, autoclave steam sterilization or can be sterile filtered using, for example, a 0.22 micron sterile filter. Sterilization employing a sterilization filter can be used when the emulsion droplet (or globule or particle) size and characteristics allows this. The droplet size distribution of the emulsion need not be entirely below the particle size cutoff of the 0.22 micron sterile filtration membrane to be sterile-filtratable. In cases wherein the droplet size distribution of the emulsion is above the particle size cutoff of the 0.22 micron sterile filtration membrane, the emulsion needs to be able to deform or change while passing through the filtration membrane and then reform after passing through. This property is easily determined by routine testing of emulsion droplet size distributions and percent of total oil in the compositions before and after filtration. Alternatively, a loss of a small amount of larger droplet sized material may be acceptable.

The oil-in-water emulsions preferably are thermodynamically stable. In some examples the emulsions may not be isotropic transparent compositions, such as microemulsions or refractive index-matched emulsions. In other, currently preferred, examples the emulsions are transparent or translucent. The emulsions of the present invention advantageously have a shelf life exceeding 30 days, or more preferably 60 days, or more preferably 90 days, or more preferably 6 months, or more preferably a year or more at room temperature.

In other examples, the compositions of the present invention may be a microemulsion. Microemulsions are a dispersion of aqueous and non-aqueous phases in the presence of a surfactant and co-surfactant in a manner that reduces surface tension at the interface between phases. These emulsions may have high stability, small droplet size (e.g., about 100 nm or less in diameter) and a transparent appearance. In contrast to ordinary emulsions, microemulsions may form upon simple mixing of the components and do not require the high shear conditions generally used in the formation of ordinary emulsions. The three basic types of microemulsions are direct (oil dispersed in water, o/w), reversed (water dispersed in oil, w/o) and bicontinuous. The aqueous phase may contain salts, while the hydrophobic phase may comprise more than one oil.

For example, the oils may comprise one or more naturally occurring wax or oil. In particularly preferred example, the hydrophobic phase of an emulsion or microemulsion comprises jojoba "oil", which is actually a liquid wax composed of long chain wax esters, or an avocado oil. Either of these oils may be present as the only oil in a therapeutic composition, or may be combined with one or more additional (preferably plant-based) oil.

The components of the jojoba wax esters include long chain alcohols esterified with long chain fatty acids with a total of 38 to 44 carbon atoms. Exemplary long chain fatty acids include gadoleic, palmitic, palmitoleic, stearic, oleic, linoleic, arachidic, linolenic, eicosenoic, behenic, erucic, lignoceric, lactic, decate, acetic and myristic fatty acids. The fatty acids typically have carbon chains of $C_{12}$ to $C_{30}$, with or without various degrees of saturation or unsaturation. The alcohol components of the wax ester contain carbon chains between $C_{16}$ and $C_{32}$ with or without various degrees of saturation or unsaturation. The alcohol component may be eicos-11-enol, docos-13-enol, tetracos-15-enol, myristyl alcohol, octyldodecyl stearoyl alcohol or cetyl alcohol. Jojoba has been identified as chemically similar to sperm whale oil and as having an antimicrobial activity against envelope viruses, mold, fungus and bacteria. See e.g., U.S. Pat. Nos. 4,585,656 and 6,559,182, each being hereby incorporated by reference herein.

Avocado oil is about 71% (w) monosaturated fatty acids, about 13% polyunsaturated fatty acids, and about 16% saturated fatty acids, and contains palmitic, palmitoleic, stearic, oleic, linoleic and linolenic fatty acids and smaller amounts of campesterol, beta-sitosterol and stigmasterol and bio-active phytochemicals including terpenoids, glutathione, carotenoids, phenols, tannins, lecithin, sterolin. D-mannoheptulose and persenone A and B. It will be understood that these percentages may differ somewhat based upon factors that may include the variety of avocado used, the pharmaceutical grade of the avocado oil used, and the method of extraction. Clinical studies have shown that an avocado-rich diet lowers LDL-cholesterol and triglycerides and increases HDL-cholesterol compared to high carbohydrate diets or other diets without avocado in hypercholesterolemic patients.

Methods of making microemulsions are well-known in the art; some methods are disclosed in the following publications. Gerbacia and Rosano, J. Coll. & Interface Sci. (44), 242-248; Rosano, U.S. Pat. No. 4,146,499; Evitts, European Patent Publication EP 0480690 A1, and Kawashima et al., U.S. Pat. No. 6,582,718, each of which is hereby incorporated by reference herein.

The following non-limiting examples illustrate certain aspects of the present invention.

Example 1

A series of different artificial tear treatment compositions are prepared. Each of the treatment compositions in accordance with the present invention are suitable for use in treating dry eye syndrome in humans.

TABLE 1

| Component | Compositions w/v % | | | | | | | |
|---|---|---|---|---|---|---|---|---|
| | G | H | I | J | K | L | M | N |
| Jojoba Oil | 0.1 | — | — | — | 0.25 | — | 0.1 | 0.1 |
| Avocado Oil | — | 0.1 | — | — | — | 0.25 | 0.1 | 0.1 |
| Tonicity NaCl (or q.s. ad 280 to 320 mOmol | 0.68 | 0.68 | 0.68 | 0.68 | 0.68 | 0.68 | 0.68 | 0.68 |
| Polysorbate 80 | 0.05 | 0.05 | 0.05 | 0.05 | 0.05 | 0.05 | 0.05 | 0.05 |
| Glycerin | 0.5 | 0.5 | 0.5 | 0.5 | 0.5 | 0.5 | 0.5 | 0.5 |
| Pemulen ® | 0.005 | 0.005 | 0.005 | 0.005 | 0.01 | 0.01 | 0.01 | 0.01 |
| Carbopol ® 980 | — | — | — | — | — | — | — | 0.25 |
| HPMC | 0.1 | 0.1 | — | — | 0.25 | 0.25 | 0.25 | — |
| Natural Oils: Argan or Oleuropein | — | — | — | — | 0.1 | — | 0.1 | 0.1 |

TABLE 1-continued

| | Compositions w/v % | | | | | | | |
|---|---|---|---|---|---|---|---|---|
| Component | G | H | I | J | K | L | M | N |
| PEG 400 | 0.5 | 0.5 | 0.5 | 0.5 | 0.5 | 0.5 | 0.5 | 0.5 |
| NaOH/HCl | Adjust pH to 7.3 (spec. 7.2-7.4) | | | | | | | |
| Boric Acid | 0.25 | 0.25 | 0.25 | 0.25 | 0.25 | 0.25 | 0.25 | 0.25 |
| Na Borate Decahydrate | 0.4 | 0.4 | 0.4 | 0.4 | 0.4 | 0.4 | 0.4 | 0.4 |
| BAK | 0.005 | 0.005 | 0.005 | 0.005 | 0.005 | 0.005 | 0.005 | — |
| Na Chlorite | — | — | — | — | — | — | — | 0.005 |
| Purified water (or WFI) | q.s. ad 100 | | | | | | | |

As can be seen above, in certain of the exemplified compositions (e.g., Compositions G, H and L) a single oil is used, while in other compositions (Compositions K, M and N) more than one oil is used, and in still others (Compositions I and J) no oil is used. Thus, a variety of dry eye therapeutic compositions may be made, each to suit a different set of patient symptoms and tear properties. While all the compositions exemplified here contain an antimicrobial (BAK or sodium chlorite), it will be understood that preservative-free (for example, sterile) versions of these or other compositions can also be made). The concentration of viscosity inducing components (in this case compounds such as Carbopol®, Pemulen®, HPMC and PEG) can be varied as needed.

Although the compositions of the present invention are not limited thereto, in preferred examples the range of viscosities of the series of therapeutic compositions is about 3, 5, 7, 10, 15 and 20 centipoise (cP), the specific gravity of each of the compositions is between about 0.7 and about 1.1; the refractive index of each of the compositions is between about 1.20 to about 1.8, with a most preferred range being about 1.33-about 1.57.

Example 2

A group of patients, each of whom is indicating that he/she is experiencing some degree of eye discomfort, are assembled selected for testing to determine the presence or absence of dry eye syndrome.

The testing is conducted by qualified medical personnel who are experienced in recognizing the presence and severity of dry eye syndrome in a patient's eye(s). Tears are collected from, the amount of tears determined, and quality of the tears are analyzed for pH, osmolality, protein content, hydrophobic/hydrophilic balance, and viscosity and compared to average values for subjects unaffected by dry eye syndrome.

As a result of this testing, it is determined that some of the people do not have dry eye syndrome and that others do have dry eye syndrome. In particular, among the people who are identified as having dry eye syndrome subgroups can be identified.

Subgroup A patients have subnormal quantity of tears, but normal levels of protein, indicating that the mucoid (viscous) layer of the tears is intact, an osmolality on the normal range, a normal ratio of hydrophobic to hydrophilic components in the tears, and a pH about 7.4. Based on these findings, an artificial tear treatment composition having the approximate pH, osmolality, ratio of hydrophobic to hydrophilic components, and viscosity of natural tears is preliminarily concluded to be potentially optimal, from the point of view of both effective treatment and patient comfort.

Subgroup B patients have subnormal quantity of tears and protein, and the viscosity of the tears is subnormal. The osmolality of the tears is in the normal range, and there is a normal ratio of hydrophobic to hydrophilic components in the tears, and a pH about 7.4. The patients report a gritty feeling in the eyes. Based on these findings, an artificial tear treatment composition having the approximate pH, osmolality, ratio of hydrophobic to hydrophilic components, and of natural tears, and increased viscosity compared to normal tears (thus permitting the tears to spread more evenly across the cornea), is preliminarily concluded to be potentially optimal, from the point of view of both effective treatment and patient comfort.

Subgroup C patients have subnormal quantity of tears. Protein and viscosity of the tears is also normal. The osmolality of the tears is equivalent to about 1.8% (w/v) sodium chloride (hypertonic). There is a normal ratio of hydrophobic to hydrophilic components in the tears; however the pH of the tears is about 6.2. The patients report a stinging sensation in the eyes. Based on these findings, an artificial tear treatment composition buffered to physiological pH (approximately 7.4) and having the approximate ratio of hydrophobic to hydrophilic components of natural tears, and slightly hypotonic (e.g., equivalent to about 0.5% (w/v) sodium chloride) compared to normal tears, is preliminarily concluded to be potentially optimal, from the point of view of both effective treatment and patient comfort.

Subgroup D patients have normal quantity of tears. Protein and viscosity of the tears is also normal. The osmolality of the tears is equivalent to about 0.5% (w/v) sodium chloride (hypotonic). There is a higher than normal ratio of hydrophobic to hydrophilic components in the tears; pH of the tears is about 7.4. The patients report a stinging sensation in the eyes. Based on these findings, an artificial tear treatment composition having a normal ratio of hydrophobic to hydrophilic components of natural tears, and slightly hypertonic (e.g., equivalent to about 1.8% sodium chloride) compared to normal tears, is preliminarily concluded to be potentially optimal, from the point of view of both effective treatment and patient comfort.

Subgroup E patients have normal quantity of tears. Protein and viscosity of the tears is suboptimal. The osmolality of the tears is equivalent to about 0.5% (w/v) sodium chloride (hypotonic). There is a higher than normal ratio of hydrophobic to hydrophilic components in the tears; pH of the tears is about 7.4. The patients report a stinging, burning sensation in the eyes. Based on these findings, an artificial tear treatment composition having a viscosity slightly higher than normal, a normal ratio of hydrophobic to hydrophilic components of natural tears, and being slightly hypertonic (e.g., equivalent to about 1.8% sodium chloride) compared to normal tears, is preliminarily concluded to be potentially optimal, from the point of view of both effective treatment and patient comfort.

Each member of the group of dry eye syndrome-positive patients is are interviewed regarding their eyes, in particular, whether their eyes are sensitive to anything, including medications and eye drops placed in the eye, whether any allergies and/or other sensitivities are known which could impact the treatment approach to dealing with dry eye syndrome.

These inquiries are sufficiently detailed to identify any specific issues that may arise or become apparent during the treatment of the person's dry eye syndrome. As a result of inquiring of the people in this manner, each of the people are identified as: (a) a person who has only minor or no comfort issues having eye drops in the eye; (b) a person who has significant comfort issues in having eye drops in the eye.

As a result of the above-noted testing and inquiring, each person who was tested and inquired about, as noted above, is provided with one of the Compositions A-E based on the results of the testing and inquiries.

The use of such a testing/inquiry approach, in combination with different treatment compositions, e.g., Compositions A-E, to treat dry eye syndrome provides a highly effective approach to treat dry eye syndrome in a way which is individually selected to treat the dry eye system while, at the same time, taking into account comfort and safety concerns of the person being treated.

Example 3

A set of different ocular skin care base compositions O through Y as presented in the table below are prepared. Each of the ocular skin care base compositions may be used alone for the conditioning and moisturizing of the skin, or alternatively as the basis for the addition of cosmetic additives such as eye shadow or eyeliner pigments and other ingredients are suitable for use in patients suffering from dry eye syndrome or to prevent eye irritation.

TABLE 3

| Component | A % (w/v) | B % (w/v) | C % (w/v) | D % (w/v) | E % (w/v) | F % (w/v) |
|---|---|---|---|---|---|---|
| Avocado Oil | 0.100 | 0.300 | 0.500 | | | |
| Jojoba Oil | | | | 0.100 | 0.300 | 0.500 |
| Glycerin | 1.00 | 1.00 | 1.00 | 1.00 | 1.00 | 1.00 |
| Polysorbate ® 80 | 0.050 | 0.075 | 0.100 | 0.050 | 0.075 | 0.100 |
| Pemulen ® TR-2 NF | 0.100 | 0.200 | 0.300 | 0.100 | 0.200 | 0.300 |
| Boric Acid | 0.600 | 0.600 | 0.600 | 0.600 | 0.600 | 0.600 |
| BAK | 0.01 | 0.01 | 0.01 | 0.01 | 0.01 | 0.01 |
| EDTA | 0.100 | 0.100 | 0.100 | 0.100 | 0.100 | 0.100 |
| 0.1N NaOH | To pH 7.4 | To pH 7.4 | To pH 7.4 | To pH 7.4 | To pH 7.4 | To pH 7.4 |
| Water | QS | QS | QS | QS | QS | QS |

Formulations are made as follows: 1.00 g of glycerin was added to 80 g of water at room temperature and mixed in a beaker with a magnetic stir bar. Pemulen® is added (For-

TABLE 2

Compositions Ocular/Derm w/v %

| Component | O | P | Q | R | S | T | U | V | W | X | Y |
|---|---|---|---|---|---|---|---|---|---|---|---|
| Jojoba Oil | 0.25 | — | — | 0.25 | 0.25 | — | 0.1 | 0.1 | — | — | — |
| Avocado Oil | — | 0.25 | — | 0.25 | — | 0.25 | 0.1 | 0.1 | 0.1 | 0.1 | 0.1 |
| Natural Oils: Argan or Oleuropein | — | — | 0.25 | 0.25 | 0.1 | — | 0.1 | 0.1 | — | — | — |
| *Simulgel ® or *Carbopol ® 980 | 0.5 | 0.5 | 0.5 | 1.0 | 1.0 | 0.5 | 0.25 | 0.25 | | | |
| Polysorbate ® 80 | 0.05 | 0.05 | 0.05 | 0.05 | 0.05 | 0.05 | 0.05 | 0.05 | 0.05 | 0.05 | 0.05 |
| Glycerin | 0.5 | 0.5 | 0.5 | 0.5 | 0.5 | 0.5 | 0.5 | 0.5 | 0.5 | 0.5 | 0.5 |
| *Pemulen ® | 0.01 | 0.01 | 0.01 | 0.01 | 0.01 | 0.01 | 0.01 | 0.01 | — | — | — |
| *HPMC | 0.1 | 0.1 | — | — | 0.25 | 0.25 | — | — | 0.1 | 0.25 | — |
| *CMC | — | — | — | — | — | — | 0.25 | 0.25 | — | — | — |
| PEG 400 | 0.5 | 0.5 | 0.5 | 0.5 | 0.5 | 0.5 | 0.5 | 0.5 | — | — | 0.5 |
| NaOH/HCl | Adjust pH to 7.3 (spec. 7.2-7.4) | | | | | | | | | | |
| Boric Acid | 0.20 | 0.25 | 0.25 | 0.25 | 0.25 | 0.25 | 0.25 | 0.25 | 0.25 | 0.25 | 0.25 |
| Na Borate Decahydrate | 0.4 | 0.4 | 0.4 | 0.4 | 0.4 | 0.4 | 0.4 | 0.4 | 0.4 | 0.4 | 0.4 |
| BAK | 0.005 | 0.005 | 0.005 | 0.010 | 0.005 | 0.005 | 0.01 | — | 0.010 | 0.010 | 0.010 |
| Na Chlorite | — | — | — | — | — | — | — | 0.01 | — | — | — |
| Tonicity NaCl (or q.s. ad 280 to 320 mOmol | 0.68 | 0.68 | 0.68 | 0.68 | 0.68 | 0.68 | 0.68 | 0.68 | 0.68 | 0.68 | 0.68 |
| NaOH/HCl | Adjust pH to 7.3 (spec. 7.2-7.4) | | | | | | | | | | |
| Purified water (or WFI) | q.s. ad 100 | | | | | | | | | | |
| Viscosity | 3-50 cP (q.s. HPMC/CMC/Carbopol ® 980, where necessary) | | | | | | | | | | |

In this example Simulgel® (a family of acrylate polymers) preparations contain Polysorbate® 80. If Sumulgel® is used, additional Polysorbate® 80 should only be added if and as necessary to reach the final concentration of 0.25% (w/v). Additionally, in these examples, the thickeners Simulgel® or Carbopol®, Pemulen®, HPMC, CMC (carboxymethyl cellulose) should be adjusted in the respective proportions to each other given here to reach the desired viscosity.

Example 4

In order to determine suitable formulation parameters, three topical ocular formulations are made to have the following final compositions:

mulations A and D: 100 mg; Formulations B and E: 200 mg; Formulations C and F: 300 mg) while continuing to mix.

Polysorbate® 80 is added (Formulations A and D: 50 mg; Formulations B and E: 75 mg; Formulations C and F: 100 mg) while continuing to mix with heating for 15 minutes, then cooling. Avocado oil is added to Formulations A (100 mg), B (300 mg) and C (500 mg) and jojoba oil to Formulations D (100 mg), E (300 mg) and F (500 mg) while continuing to mix.

20 µl of a 50% (w/v) BAK solution is added with mixing, followed by 100 mg of disodium EDTA while continuing to mix. 0.1 N NaOH is added to bring the pH of the formulation to 7.4±0.3. Finally, water is then added to bring to total volume to 100 ml.

Formulations B, C, E and F are found to be quite viscous, forming a non-pourable gel or paste with air bubbles entrapped within. Formulations A and D were light grey opaque viscous liquids.

Example 5

The high viscosity of Formulations A-F of Example 4 is surprising, particularly given the low Pemulen® concentrations; a new set of formulations containing lower amounts of Pemulen® and varying the order of addition of the components is made. Additionally, mixing is done using an IKA overhead mixer rather than by using magnetic stir plates and stir bars.

Three formulations (G, G1 and H) are made using previous formulations A and D as starting points. Formulations G and G1 contain avocado oil and other ingredients in identical amounts, but differ in the order of addition of Pemulen®. Formulation H contains jojoba oil.

TABLE 4

| Component | G<br>% (w/v) | G1<br>% (w/v) | H<br>% (w/v) |
|---|---|---|---|
| Avocado Oil | 0.100 | 0.100 | |
| Jojoba Oil | | | 0.1 |
| Glycerin | 1.00 | 1.00 | 1.00 |
| Polysorbate ® 80 | 0.05 | 0.05 | 0.05 |
| Pemulen ® TR-2 NF | 0.01 | 0.01 | 0.01 |
| Boric Acid | 0.60 | 0.60 | 0.60 |
| BAK | 0.01 | 0.01 | 0.01 |
| EDTA | 0.10 | 0.10 | 0.10 |
| 0.1N NaOH | To pH 7.4 | To pH 7.4 | To pH 7.4 |
| Water | QS | QS | QS |

All formulations are initiated with 800 g of water in a beaker. The IKA mixer shaft and impeller is inserted into the samples and the mixing speed adjusted to 375 rpm (sufficient to draw floating material below the surface without splashing, while minimizing the amount of air drawn into the mixture).

For Formulation G, the order of ingredients is: glycerin, Polysorbate® 80, avocado oil, boric acid, BAK, EDTA and 1 N NaOH to pH 7.4; all ingredients are added with mixing. Pemulen® is then added (10 ml of a 1 mg/ml solution in water). Water is then added to a final volume of 1000 ml.

Formulation G1 is prepared in the same manner as Formulation G1, except Pemulen® is added following the addition of EDTA; the pH of the mixture is then adjusted with 1 N NaOH to pH 7.2 and brought to volume (1000 ml) with water.

Formulation H is prepared in the same manner as Formulation G, except that jojoba oil is substituted for avocado oil.

Immediately upon mixing Formulation G 1 appears to be the most uniform dispersion, lacking observable undissolved particles or solids as seen in both Formulations G and H. Formulation G1 has a viscosity of 1.1 cP, a surface tension of 31 dynes/cm and a percent transmittance at 580 nm of 4.4.

The samples are divided into aliquots and incubated at 25° C. and 40° C. for 2 weeks, and observed at time 0, one week and 2 weeks. pH, osmolality and viscosity remain unchanged in all samples at both temperatures.

Example 6

Formulation G1 is accessed as the superior candidate artificial tear formulation in Example 5 with respect to appearance and viscosity. Two further formulations, G2 and I, are made based upon the results of Example 5; these formulations are made using avocado oil to preserve experimental rigor and congruency with Example 5; however, Applicants believe that similar results can be obtained using other oils with little or no additional experimentation. As in Example 5, mixing is done using an IKA overhead mixer rather than by using magnetic stir plates and stir bars.

Formulation G2 is made in a 1 liter beaker (("aqueous phase" Beaker A); 700 g of water are added. Boric acid and EDTA are added with mixing at 348 rpm; the pH of the mixture is then adjusted to pH 7.4 with 1 N NaOH.

In a separate beaker ("oil phase" Beaker B) 500 mg of Polysorbate 80 is added to 100 g water and mixed until dissolved. 10 mg of Pemulen® is added while mixing at 348 rpm; when the Pemulen® is dissolved, 200 µl of a 50% (w) BAK solution in water is added while mixing, followed by 10 g glycerin and 1 g of avocado oil.

The Contents of Beaker B are added to Beaker A while mixing at 380 rpm, and mixing continued overnight at room temperature. The pH was measured and 1 N NaOH added to adjust pH to 7.37, then the mixture was then transferred to a volumetric flask and water added to 1 liter.

Formulation I is made as follows:

A 1 mg/g Pemulen solution is made in water. About 80 g water is added to a beaker and 100 mg Pemulen is added and mixed using a magnetic stir bar until dissolved, then brought to 100 g with water.

In a separate beaker about 25 g of water is given 500 mg Polysorbate® 80 and mixed with a stirbar so as not to incorporate air into the solution.

10 g of the Pemulen® solution is transferred to a small beaker with a stirbar, and the solution stirred while adding 250 µl (250 mg) of 18% NaOH. The Pemulen® is added to the NaOH at this stage in an attempt to cause some limited hydrolysis of the Pemulen® in order to reduce the viscosity of the solution somewhat before incorporation into the oil phase. A homogeneous mixture was not obtained at this stage without mixing. The solution was then mixed with heat for 90 minutes. A solution was maintained at about 40° C. One g of avocado oil was gently warmed to about 30° C., then added to the Pemulen® solution with mixing. Mixing is continued until a smooth homogeneous solution is formed. The temperature is maintained at 25° C.-30° C.

A boric acid buffer is prepared by adding 800 g of water to a 1 liter beaker, then the following ingredients were added in sequence: 1 g glycerin, 6 g boric acid, 1 g EDTA, 1 N NaOH to adjust pH to 7.39. The entire contents of the Polysorbate® solution is then added, with mixing. The warm Pemulen®/oil mixture is then added to the buffer solution under moderate agitation, and the beaker rinsed with the buffer solution. Finally, 100 mg of BAK is added from a 50% BAK stock solution, and the final pH determined to be 7.59. The final concentrations of ingredients are as set forth in Table 5.

TABLE 5

| Ingredient | Form. G-2<br>(% w/v) | Form. I<br>(% w/v) |
|---|---|---|
| Avocado Oil | 0.1 | 0.1 |
| Glycerin | 1 | 1 |
| Polysorbate 80 | 0.05 | 0.05 |
| Pemulen TR-2 NF | 0.01 | 0.01 |
| Boric acid | 0.6 | 0.6 |
| BAK | 0.01 | 0.01 |
| EDTA, disodium, dihydrate | 0.1 | 0.1 |
| NAOH | — | 0.0045 |

TABLE 5-continued

| Ingredient | Form. G-2 (% w/v) | Form. I (% w/v) |
|---|---|---|
| 1N NaOH | To pH 7.4 | To pH 7.4 |
| Water | QS | QS |

The appearance of Formulation G2 and I is similar. Both are light grey cloudy solutions having undissolved white particles. Of the two formulations, Formulation I contains smaller particles, while Formulation G2 contains both large and small particles.

Example 7

It is assessed that the results obtained with Formulations G2 and I indicate that a reduction in BAK concentration may be possible, and may assist the formulation stability. The order of addition of components will also be modified by making a stock solution of Pemulen® in borate buffer to add to the other ingredients, and the components will be mixed using a Silverson high speed mixer with an emulsion screen to aid in the emulsification process.

Six liters of 0.6% (w) borate buffer are made as follows. 4.8 liters of water is given 36 g boric acid while stirring, and the pH adjusted to approximately 7.3 using 1 N NaOH. The buffer is then brought to 6 liters with additional water.

Preparation of Formulation

A 4 liter beaker is given 1.6 g of the 0.6% (w) borate buffer and mixed with 20 g glycerin using a magnetic stir bar. 1 g of Polysorbate® 80 is added with continued mixing. 2 g of disodium EDTA dihydrate is added with mixing. When all components are visually dissolved, the magnetic stirrer is taken away, and the Silverson mixer's emulsion mixing screen is inserted into the solution. The speed of the Silverson mixer is adjusted so as to draw floating material under the surface without splashing, and to minimize air being drawn into the water.

Two g of avocado oil is then added with mixing. A Pemulen® solution (0.02 g/g) is made using 400 g of the 0.6% (w) borate buffer to dissolve 10 g of Pemulen®, then the solution brought to 500 g using e 0.6% (w) borate buffer. Ten g of the 0.02% (W) Pemulen® solution is added to the mixture of the other ingredients with mixing.

0.2 ml of a 50% (w) BAK solution is added to the mixture, yielding a final BAK concentration of 0.005% (w). The mixture is then brought to 2 liters using the 0.6% (w) borate buffer.

Preparation of Formulation K

Formulation K is prepared in the same manner as Formulation J, except that 30 g of the 0.02% (w) Pemulen® borate buffer solution is added to the mixture of water, glycerin, EDTA Polysorbate® 80 and avocado oil, with mixing, as described with respect to Formulation J. 0.2 ml of a 50% (w) BAK solution is added to this mixture, yielding a final BAK concentration of 0.005% (w). The mixture is then brought to 2 liters using the 0.6% (w) borate buffer.

Preparation of Formulation L

Formulation L is prepared in the same manner as Sample J, except that 50 g of the 0.02% (w) Pemulen® borate buffer solution is added to the mixture of water, glycerin, EDTA Polysorbate® 80 and avocado oil, with mixing, as described with respect to Formulation J. 0.2 ml of a 50% (w/v) BAK solution is then added to this mixture, yielding a final BAK concentration of 0.005% (w). The mixture is brought to 2 liters using the 0.6% (w) borate buffer.

The final concentrations of ingredients are as set forth in Table 6.

TABLE 6

| Ingredient | Form. J (% w/v) | Form. K (% w/v) | Form. L (% w/v) |
|---|---|---|---|
| Avocado Oil | 0.1 | 0.1 | 0.1 |
| Glycerin | 1 | 1 | 1 |
| Polysorbate 80 | 0.05 | 0.05 | 0.05 |
| Pemulen TR-2 NF | 0.01 | 0.03 | 0.05 |
| Boric acid | 0.6 | 0.6 | 0.6 |
| BAK | 0.005 | 0.005 | 0.005 |
| EDTA, disodium, dihydrate | 0.1 | 0.1 | 0.1 |
| 1N NaOH | To pH 7.4 | To pH 7.4 | To pH 7.4 |
| Water | QS | QS | QS |

These formulations are then tested for stability at time 0 and after one week and two weeks at 25° C. and 40° C.

Example 8

The exemplary formulations listed below in Table 7 are made and mixed substantially as set forth in Example 7:

TABLE 7

| Ingredient | Form. 1 (% w/v) | Form. 2 (% w/v) | Form. 3 (% w/v) | Form. 4 (% w/v) | Form. 5 (% w/v) | Form. 6 (% w/v) | Form. 7 (% w/v) |
|---|---|---|---|---|---|---|---|
| Menthol Oil | 0.1 | | | | | | |
| Eucalyptus Oil | | 0.1 | | | | | |
| Fennel Oil | | | 0.1 | | | | |
| Bergamot Oil | | | | 0.1 | | | |
| Sesame Oil | | | | | 0.1 | | |
| Peppermint Oil | | | | | | 0.1 | |
| Jojoba Oil | | | | | | | 0.1 |
| Glycerin | 1 | 1 | 1 | 1 | 1 | 1 | 1 |
| Polysorbate 80 | 0.05 | 0.05 | 0.05 | 0.05 | 0.05 | 0.05 | 0.05 |
| Pemulen TR-2 NF | 0.03 | 0.03 | 0.03 | 0.03 | 0.03 | 0.03 | 0.03 |
| Boric acid | 0.6 | 0.6 | 0.6 | 0.6 | 0.6 | 0.6 | 0.6 |
| BAK | 0.005 | 0.005 | 0.005 | 0.005 | 0.005 | 0.005 | 0.005 |
| EDTA, disodium, dihydrate | 0.1 | 0.1 | 0.1 | 0.1 | 0.1 | 0.1 | 0.1 |

TABLE 7-continued

| Ingredient | Form. 1 (% w/v) | Form. 2 (% w/v) | Form. 3 (% w/v) | Form. 4 (% w/v) | Form. 5 (% w/v) | Form. 6 (% w/v) | Form. 7 (% w/v) |
|---|---|---|---|---|---|---|---|
| 1N NaOH | To pH 7.4 | To pH 7.4 | To pH 7.4 | To pH 7.4 | To pH 7.4 | To pH 7.4 | To pH 7.4 |
| Water | QS | QS | QS | QS | QS | QS | QS |

Example 9

Stock solutions of 0.04% mg/ml Pemulen™ and 8 mg/ml Hypromellose™ (hydroxypropylmethylcellulose) are prepared by incorporating the polymers into hot DI water. The stock solutions are then stored at 5° C. overnight.

The oil phases of Formulation T and Formulation U are prepared by mixing the oils with hot polysorbate 80 at 55° C. to 65° C. The oil phases are then emulsified with 40 mg/ml aqueous solution of glycerin using a Silverson high shear mixer for about 1 hour at 55° C. to 65° C., to achieve a homogenous emulsion. The remaining aqueous components and the Pemulen™ and Hypromellose™ are added by mixing into the homogeneous emulsions to form Formulation T and Formulation U. Formulation T, which contains avocado oil as the sole oil, is a uniform opaque emulsion having a white foam on the top[surface. Formulation U, which contains avocado oil and castor oil, is a uniform translucent emulsion showing no surface foam.

Thus, not only is the clarity of Formulation U greatly increased compared to Formulation T, but there is a slight decrease in viscosity when 0.1% avocado oil is replaced in an otherwise identical Formulation U with a 0.05% avocado oil and 0.05% castor oil. Otherwise the tested physiochemical characteristics of the two formulations are similar.

Additionally, the presence of castor oil (e.g., Formulation O) provides a decrease in surface tension compared to single oil formulations M, Q and R. Interestingly, adding castor oil as a second oil component (i.e. formulation N which also contained jojoba oil) similarly achieves a reduction in surface tension. Noteworthy, is that the surface tension data for formulations O (castor oil only) and N (jojoba with castor oil) achieve equivalent surface tension lowering, and suggests that the addition of castor oil may have a predominant, governing effect on surface tension whether used singly or in combinations with other oils, such as plant-based oils such as avocado oil and jojoba oil.

TABLE 8

| Ingredient | Form. M % w/v | Form. N % w/v | Form. O % w/v | Form. P % w/v | Form. Q % w/v | Form. R % w/v | Form. T % w/v | Form. U % w/v |
|---|---|---|---|---|---|---|---|---|
| Avocado Oil | 0.1 | | | | 0.1 | 0.1 | 0.1 | 0.05 |
| Jojoba Oil | | 0.1 | | | | | | |
| Castor Oil | | 0.1 | 0.1 | 0.1 | | | | 0.05 |
| Glycerin | 1 | 1 | 1 | 1 | 1 | 1 | 1 | 1 |
| Polysorbate 80 | 0.05 | 0.05 | 0.05 | 0.05 | 0.05 | 0.05 | 0.4 | 0.4 |
| Pemulen TR-2 NF | 0.01 | 0.03 | 0.05 | 0.05 | 0.002 | 0.002 | 0.01 | 0.01 |
| Hypromellose | | | | | 0.2 | 0.2 | 0.2 | 0.2 |
| Boric acid | 1.2 | 1.2 | 1.2 | 1.2 | 1.2 | 1.2 | 1.1 | 1.1 |
| Sodium perborate monohydrate | | | | | 0.02 | 0.02 | 0.02 | 0.02 |
| BAK | 0.005 | 0.005 | 0.005 | 0.005 | | | 0 | 0 |
| EDTA, disodium, dihydrate | 0.1 | 0.1 | 0.1 | 0.1 | | | 0.1 | 0.1 |
| 1N NaOH | To pH 7.4 | To pH 7.4 | To pH 7.4 | To pH 7.4 | To pH 7.4 | To pH 7.4 | To pH 7.4 | To pH 7.4 |
| Water | QS to 2 L | QS to 2 L | QS to 2 L | QS to 2 L | QS to 2 L | QS to 2 L | QS to 2 L | QS to 2 L |

These formulations are tested for pH, osmolality, surface tension and % transmittance (clarity), and the results are summarized below.

Example 10

As a model of a prospective suite of therapeutic compositions to be used with the methods of the present invention,

| Test | Form. M | Form. N | Form. O | Form. P | Form. Q | Form. R | Form. T | Form. U |
|---|---|---|---|---|---|---|---|---|
| pH | 7.4 | 7.4 | 7.4 | 7.4 | 7.1 | 7.2 | 7.7 | 7.7 |
| | | | | | 7.1 | 7.2 | 7.7 | 7.7 |
| Osmolality (mOsm/kg) | N/A | N/A | N/A | N/A | 293 | 294 | 2.86 | 287 |
| Viscosity (cP) | 1.30 | 1.33 | 1.36 | 1.40 | 4.74 | 4.70 | 4.6 | 4.35 |
| % Transmittance at 578 nm | 13.5 | 10.3 | 11.3 | 10.3 | 4.2 | 5.9 | 3.8 | 97.9 |
| Surface Tension | 40.3 | 37.2 | 36.3 | 36.6 | 48.3 | 49.3 | 46.2 | 45.9 | results obtained using selected tested therapeutic compositions G-1, M, N, O, P, Q, R, T and U, were tabulated, along with the viscosity (N), surface tension (ST) and Clarity (Percent Transmittance at 580 nm) parameters determined for these compositions. As explained in detail above, patient tolerability was determined to be proportional to Clarity/N, while therapeutic healing effect was determined to be proportional to N/ST.

| Formulation (& oil type) | Viscosity (cP) | Surface Tension (dynes/cm) | Clarity (Percent Transmittance At 580 nm) |
|---|---|---|---|
| G-1 (avocado) | 1.1 | 31 | 4.4 |
| M (avocado) | 1.3 | 40.3 | 13.5 |
| N (jojoba, castor) | 1.33 | 37.2 | 10.3 |
| O (castor) | 1.36 | 36.3 | 11.3 |
| P (castor) | 1.4 | 36.6 | 10.3 |
| Q (avo) | 4.74 | 48.3 | 4.2 |
| R (avo) | 4.7 | 49.3 | 5.9 |
| T (avo) | 4.6 | 46.5 | 3.8 |
| U (avo + castor) | 4.35 | 46.5 | 97 |

Thus, among these formulations, all are low viscosity (less than about 15 cP), making all of them either Formulation A or Formulation C based on viscosity alone.

Formulations G-1, N, O, and P are all of low surface tension. Thus, these Formulations fall under Matrix Formulation C based on low surface tension and low viscosity. Formulation M is on the edge of normal versus low surface tension.

Formulations Q, R, T and U all have higher than normal surface tension, and would tend to fall within Matrix Formulation A based on normal surface tension and low viscosity.

These formulations (G-1, M, N, O, P, Q R, T and U) may be altered further to treat patients whose symptoms and signs place their optimal therapeutic formulation within Matrix Quadrants B or D by increasing viscosity and/or decreasing surface tension (e.g., by increasing the oil concentration of the formulation). Deceased surface tension of the tear aids in the spreadability of the drop over the ocular surface, and increasing the tear breakup time.

The foregoing examples are simply for the purpose of illustration of various examples incorporating elements disclosed in the present specification. To the extent that a plurality of inventions may be disclosed herein, any such invention shall be understood to have disclosed herein alone, in combination with other features or inventions disclosed herein, or lacking any feature or features not explicitly disclosed as essential for that invention. For example, the inventions described in this specification can be practiced within elements of, or in combination with, other any features, elements, methods or structures described herein. Additionally, features illustrated herein as being present in a particular example are intended, in other examples of the present invention, to be explicitly lacking from the invention, or combinable with features described elsewhere in this patent application, in a manner not otherwise illustrated in this patent application or present in that particular example. The scope of the invention shall be determined solely by the language of the claims.

Thus, the various descriptions of the invention provided herein illustrate presently preferred examples of the invention; however, it will be understood that the invention is not limited to the examples provided, or to the specific configurations, shapes, and relation of elements unless the claims specifically indicate otherwise. Based upon the present disclosure a person of ordinary skill in the art will immediately conceive of other alternatives to the specific examples given, such that the present disclosure will be understood to provide a full written description of each of such alternatives as if each had been specifically described.

Claim terms shall be intrinsically defined not only by a specific definition in the specification, but also with reference to the Figures as understood by a person of ordinary skill in the art in light of the present disclosure.

Every publication and patent document cited herein is each hereby individually incorporated by reference in its entirety for all purposes to the same extent as if each were individually denoted.

What is claimed is:

1. A composition for applying to an eye or eyelid of a human comprising:
   water; and
   0.1% (w/v) to 0.3% (w/v), inclusive, of a hydrophobic component, wherein the hydrophobic component comprises from about 0.05% (w/v) to about 0.25% (w/v) avocado oil and from about 0.05% (w/v) to about 0.25% (w/v) castor oil, and
   at least one additional component selected from the group consisting of: an emulsifier component, a surfactant component, a tonicity component, a polyelectrolyte component, an emulsion stability component, a viscosity-enhancing component, a demulcent component, an anti-oxidant component, a pH adjustment component, a buffer component, and a preservative component,
   the hydrophobic component being present in an amount effective to provide a benefit to an eye or eyelid of a human.

2. The composition of claim 1 in which said at least one additional component comprises a first viscosity-enhancing component having a negative charge.

3. The composition of claim 2 in which said at least one additional component further comprises a emulsion stability component.

4. The composition of claim 3 in which said first viscosity-enhancing component comprises a polymer of acrylic acid, and the emulsion stability component is a non-ionic surfactant.

5. The composition of claim 1 containing
   a) from about 0.05% to about 0.01% by weight of a crosslinked co-polymer of acrylic acid and alkyl acrylate, and
   b) from about 0.05% to about 1.5% by weight of a non-ionic surfactant.

6. The composition of claim 1 wherein the viscosity-enhancing component comprises a cellulose polymer selected from the group consisting of carboxymethyl cellulose (CM), methylcellulose (MC), hydroxypropyl methylcellulose (HPMC), hydroxyethyl cellulose (HEC), and hydroxypropyl cellulose.

7. The composition of claim 1 comprising, by weight, between about 0.5% and about 1% glycerin; between about 0.05% and about 1.5% polysorbate 80; between about 0.01% and about 0.05% of a crosslinked co-polymer of acrylic acid and alkyl acrylate; between about 0.01% and about 0.1% hydroxypropylmethyl cellulose; between about 0.25% and about 1.2% boric acid; and about 0.1% disodium ethylenediamine tetracetic acid (EDTA).

8. The composition of 7 wherein the avocado oil and the castor oil are each present at a concentration of about 0.05% by weight.

9. The composition of claim 8 wherein a biocidal agent is not present.

10. The composition of claim 8 further comprising a biocidal agent.

11. The composition of claim 1, wherein the at least one component comprises a tonicity component, a viscosity enhancing agent, and a surfactant.

12. The composition of claim 1, wherein the at least one component comprises glycerin, a crosslinked co-polymer of acrylic acid and alkyl acrylate, a hydroxypropyl methylcellulose, a non-ionic surfactant, and benzalkonium chloride.

13. The composition of claim 1 having a viscosity between about one 1.0 centipoise (cP) and about 2000 cP.

14. The composition of claim 13 having a viscosity less than about 250 cP.

15. The composition of claim 13 having a viscosity between about 250 centipoise (cP) and about 2000 cP.

16. The composition of claim 1 in which the avocado oil is present at a concentration of from about 0.05% (w/v) to about 0.1% (w/v).

17. The composition of claim 1 in which the castor oil is present at a concentration of from about 0.05% (w/v) to about 0.1% (w/v).

18. The composition of claim 1 in which the avocado oil is present at a concentration of about 0.05% (w/v) to about 0.1% (w/v) and the castor oil is present at a concentration of about 0.05% (w/v) to about 0.1% (w/v).

19. The composition of claim 1 comprising an artificial tear.

20. The composition of claim 1 comprising an eyelid treatment composition.

21. The composition of claim 1, wherein the at least one additional component comprises a viscosity enhancing agent.

22. The composition of claim 21, wherein the viscosity enhancing agent comprises methylcellulose (MC), carboxymethylcellulose (CMC), hydroxypropyl methylcellulose (HPMC), hydroxyethyl cellulose (HEC), hyaluronic acid salts, or combinations thereof.

* * * * *

UNITED STATES PATENT AND TRADEMARK OFFICE
CERTIFICATE OF CORRECTION

| | |
|---|---|
| PATENT NO. | : 11,622,982 B2 |
| APPLICATION NO. | : 16/638546 |
| DATED | : April 11, 2023 |
| INVENTOR(S) | : Scott Whitcup et al. |

It is certified that error appears in the above-identified patent and that said Letters Patent is hereby corrected as shown below:

On the Title Page

Item (71), in the Applicant section, please delete "Akrivista, LLC, Corona Del Mar, CA (US)" and insert -- Akrivista LLC, Irvine, CA (US) --.

Item (73), in the Assignee section, please delete "Akrivista, LLC, Corona Del Mar, CA (US)" and insert -- Akrivista LLC, Irvine, CA (US) --.

Signed and Sealed this
Seventeenth Day of October, 2023

*Katherine Kelly Vidal*

Katherine Kelly Vidal
*Director of the United States Patent and Trademark Office*